US012809403B2

(12) United States Patent
Ariyama et al.

(10) Patent No.: US 12,809,403 B2
(45) Date of Patent: Nov. 24, 2026

(54) MOVEABLE BODY CONTROL DEVICE AND STORAGE MEDIUM

(71) Applicant: GE Precision Healthcare LLC, Waukesha, WI (US)

(72) Inventors: Naoki Ariyama, Hino (JP); Kentaro Ogata, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 68 days.

(21) Appl. No.: 19/074,163

(22) Filed: Mar. 7, 2025

(65) Prior Publication Data

US 2025/0284299 A1 Sep. 11, 2025

(30) Foreign Application Priority Data

Mar. 7, 2024 (JP) ................................ 2024-035146

(51) Int. Cl.
*G05D 3/18* (2006.01)
*A61B 6/00* (2024.01)
(Continued)

(52) U.S. Cl.
CPC ................ *G05D 3/18* (2013.01); *A61B 6/04* (2013.01); *A61B 6/54* (2013.01); *A61B 6/547* (2013.01); *A61B 6/589* (2013.01); *G03B 42/02* (2013.01); *G05D 9/12* (2013.01); *G05D 27/02* (2013.01); *G06F 3/0484* (2013.01); *G06F 3/04847* (2013.01); *G06F 3/0489* (2013.01)

(58) Field of Classification Search
CPC .. A61B 6/04; A61B 6/54; A61B 6/547; A61B 6/589; G03B 42/02; G05D 3/18; G05D 9/12; G05D 27/02; G06F 3/0484; G06F 3/04847; G06F 3/0489
See application file for complete search history.

(56) References Cited

U.S. PATENT DOCUMENTS

2006/0120515 A1 * 6/2006 Ariyama ............. A61B 6/0487 378/209

FOREIGN PATENT DOCUMENTS

JP S61290204 A 12/1986
JP H0376700 B2 12/1991
(Continued)

OTHER PUBLICATIONS

JP application 2024-035146 filed Mar. 7, 2024—Decision of Refusal issued Feb. 19, 2025; Machine Translation; 7 pages.
(Continued)

*Primary Examiner* — Mark R Gaworecki

(57) ABSTRACT

A device includes a unit including a cylinder and a piston, a subject support unit that moves in accordance with relative movement of the cylinder and the piston, a control board that generates a control signal including a first pulse width based on an operation signal input by a user operation, and an oil amount adjustment unit that adjusts the amount of oil contained in the cylinder based on the first pulse width, wherein the control board determines a value of a gain based on a deviation, calculates a second pulse width based on the deviation and the determined gain value, and generates a control signal including the second pulse width when the next operation signal is input, and the oil amount adjustment unit adjusts the amount of oil in the cylinder based on the second pulse width.

16 Claims, 17 Drawing Sheets

(51) Int. Cl.

| | |
|---|---|
| ***A61B 6/04*** | (2006.01) |
| ***A61B 6/58*** | (2024.01) |
| ***G03B 42/02*** | (2021.01) |
| ***G05D 9/12*** | (2006.01) |
| ***G05D 27/02*** | (2006.01) |
| ***G06F 3/0484*** | (2022.01) |
| ***G06F 3/04847*** | (2022.01) |
| ***G06F 3/0489*** | (2022.01) |

(56) References Cited

FOREIGN PATENT DOCUMENTS

| | | | |
|---|---|---|---|
| JP | H0949542 | A | 2/1997 |
| JP | 2006158583 | A | 6/2006 |
| JP | 2014161392 | A | 9/2014 |

OTHER PUBLICATIONS

JP2006158583 English Abstract; Espacenet.com; May 19, 2025; 1 page.

JPH0949542 English Abstract; Espacenet.com; May 19, 2025; 1 page.

JPS61290204 English Abstract, Espacenet.com; May 19, 2025; 1 page.

* cited by examiner

MOVEABLE BODY CONTROL DEVICE AND STORAGE MEDIUM

CROSS-REFERENCE TO RELATED APPLICATIONS

This application claims priority to Japanese Application No. 2024-035146, filed on Mar. 7, 2024, the disclosure of which is incorporated herein by reference in its entirety.

TECHNICAL FIELD

The present invention relates to a movable body control device that controls a movable body, and a storage medium that stores instructions for operating the movable body control device.

BACKGROUND

A CT system is known as a medical device that noninvasively images a subject. CT systems can acquire tomographic images of a subject in a short scanning time and therefore are widely used in hospitals and other medical facilities.

The CT system applies a prescribed voltage to a cathode-anode tube of an X-ray tube to generate X-rays. The generated X-rays penetrate the subject and are detected by a detector. The CT system reconstructs a CT image of the subject on the basis of data detected by the detector.

SUMMARY

When imaging a subject using a CT system, a subject is laid on a table. After the subject is laid on the table, an operator adjusts the height of the table so that the region of the subject for imaging is appropriately positioned in the bore of the gantry.

When adjusting the table height, an operator typically makes a coarse adjustment to the table height and then makes a fine adjustment to the table height. Inching is a known method of fine adjustment. A CT system configured to allow fine adjustment by inching is provided with a control panel that enables an operator to finely adjust the height of the table. When the operator operates the control panel, the table height is fine-tuned in response to the operation.

The mechanism for raising and lowering the table generally uses hydraulic or electric servo motors. Electric servo motors are good at fine adjustments and high-precision control, but are not good at generating large forces and are expensive. On the other hand, hydraulic motors are inexpensive and good at generating large forces, but have the disadvantage of being difficult to adjust finely. Hydraulic systems are often used for the tables of CT systems where price is a priority. The hydraulic mechanism uses valves to adjust the flow rate of the working fluid (oil). When an operator operates the control panel, the valves open and close to adjust the table height. However, with a hydraulic mechanism, when an operator operates the control panel once, the amount of change in table height corresponding to one operation of the control panel may deviate from the desired value (target change amount). As a result, the operator must operate the control panel multiple times to match the table height to the desired position, which takes time to adjust the table height and increases the workload of the operator. To alleviate this problem as much as possible, the current practice is to adjust the valve flow rate for each table during the final stage of table manufacturing inspection. However, the flow rate of the valve is adjusted only under specific conditions (for example, temperature conditions and the like). Therefore, when the table height is adjusted under conditions other than the specified conditions, there is a problem that the operator must operate the control panel multiple times to match the table height to the desired position. Furthermore, by adjusting the flow rate of the valve during table manufacturing inspection, the amount of change in table height will initially match the desired value (target change amount), but as the table continues to be used, there is a possibility that the change will gradually deviate from the desired value (target change amount), and there is a limit to the extent that the valve flow rate can be adjusted during table manufacturing inspection. To address this problem, tables using hydraulic servo motors are known, but using a hydraulic servo mechanism is not realistic in a table that is required to be inexpensive.

Furthermore, some CT systems are known to be equipped with an inclination mechanism that can incline the gantry. If hydraulic motors are used in this inclination mechanism, the operator may have to operate the control panel multiple times to match the inclination angle of the gantry to the desired inclination angle, which again places a heavy burden on the operator.

Therefore, a technique is desired that allows easy adjustment of a movable body such as a gantry, table, and the like.

A first aspect of the present invention is a movable body control device, containing a unit including a cylinder and a piston, at least a portion of the piston being provided in the cylinder, and configured to move one of the cylinder and the piston relative to the other by adjusting an amount of a working fluid in the cylinder; a movable body that moves in response to relative movement of the cylinder and the piston; a control unit that generates a control signal including a first pulse width corresponding to a target change amount so that the movable body moves by the target change amount, based on a first operation signal input by a user operation, the first operation signal provided for moving the movable body by the target change amount; and a fluid amount adjusting unit that adjusts the amount of the working fluid contained in the cylinder based on the first pulse width; wherein the control unit determines an amount of movement of the movable body by adjusting the amount of working fluid in the cylinder; determines a gain value based on a deviation between the amount of movement of the movable body and the target amount of change; calculates a second pulse width based on the deviation and the determined gain value; and generates a control signal including the second pulse width when a second operation signal for moving the movable body by a target change amount is input after the first operation signal; and the fluid amount adjusting unit adjusts the amount of working fluid in the cylinder based on the second pulse width.

Furthermore, a second aspect of the present invention is a non-transitory computer-readable storage medium included in a movable body control device or capable of communicating with the movable body control device, wherein the moveable body control device includes a unit including a cylinder and a piston, at least a portion of the piston being provided in the cylinder, and configured to move one of the cylinder and the piston relative to the other by adjusting an amount of a working fluid in the cylinder; a movable body that moves in response to relative movement of the cylinder and the piston; a control unit that generates a control signal including a first pulse width corresponding to a target change amount so that the movable body moves by the target change amount, based on a first operation signal input by a user operation, the first operation signal provided for moving the movable body by the target change amount; and a fluid amount adjusting unit that adjusts the amount of the working fluid contained in the cylinder based on the first pulse width; wherein the control unit includes one or more processors; the instructions contained in the memory, when executed by the one or more processors, cause the one or more processors to determine an amount of movement of the movable body by adjusting the amount of working fluid in the cylinder; determine a gain value based on a deviation between the amount of movement of the movable body and the target change amount; calculate a second pulse width based on the deviation and the determined gain value; and generate a control signal including the second pulse width when a second operation signal for moving the movable body by a target change amount is input after the first operation signal; and the fluid amount adjusting unit adjusts the amount of working fluid in the cylinder based on the second pulse width.

In the present invention, the gain value corresponding to the target change amount is determined based on the deviation between the amount of movement of the movable body and the target change amount. Therefore, since the gain value is determined taking into consideration the actual deviation, a second pulse width that reduces the deviation between the actual displacement amount of the movable body and the target change amount can be calculated by using the determined gain value. Furthermore, when the second operation signal is input, the amount of movement of the movable body is adjusted based on the control signal including the second pulse width, so the amount of movement of the movable body can be brought sufficiently close to the target change amount, thereby reducing the workload of the user when adjusting the movable body.

DETAILED DESCRIPTION OF THE DRAWINGS

An embodiment for carrying out the invention will be described below, but the present invention is not limited to the following embodiment.

Figure 1:
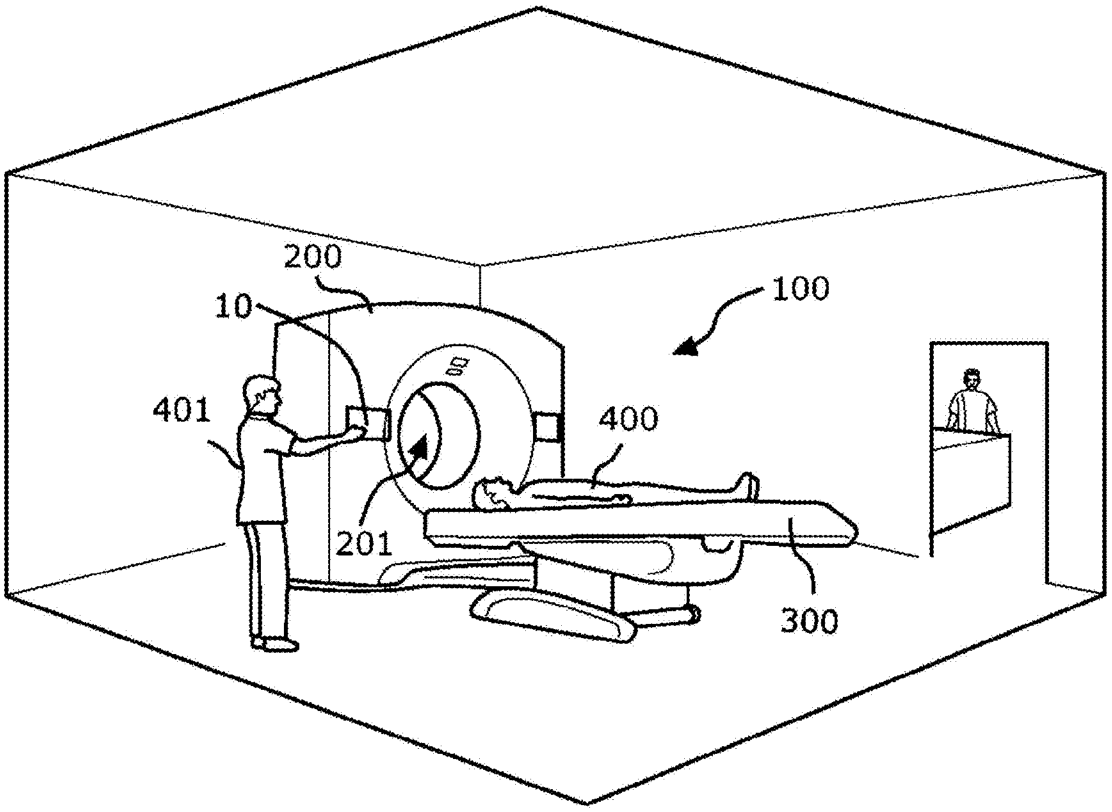
FIG. 1 is a perspective view of the CT system 100 of Embodiment 1.

FIG. 1 is a perspective view of a CT system 100 of Embodiment 1. The CT system 100 includes a gantry 200 and a table 300. The gantry 200 and the table 300 are installed in a scan room. The gantry 200 includes a bore 201. A subject 400 is transported through the bore 201 and then the subject 400 is scanned. Furthermore, an operation panel 10 that can be operated by an operator 401 is attached to the front surface of the gantry 200 (see FIG. 2).

Figure 2:
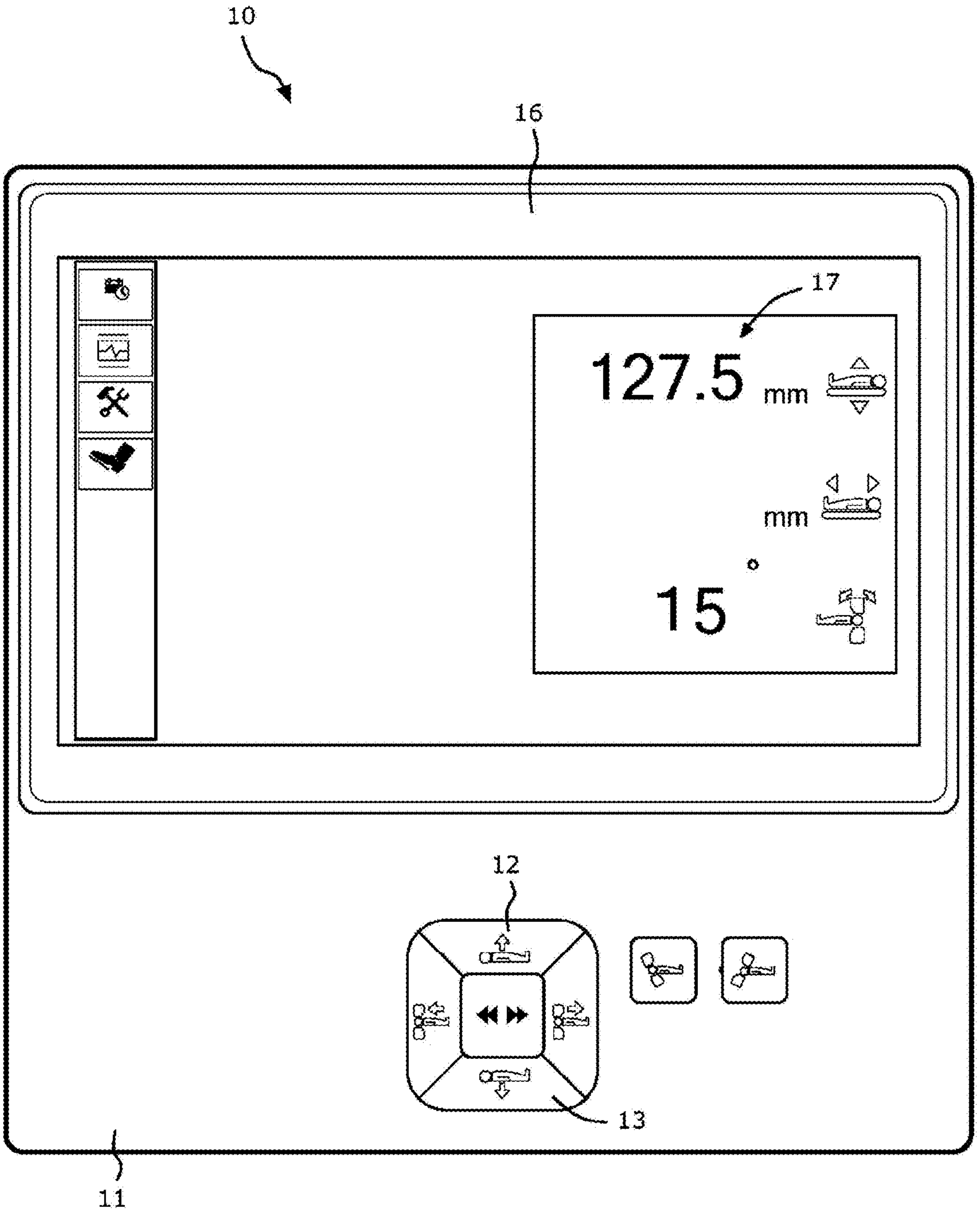
FIG. 2 is an enlarged view of the operation panel 10.

FIG. 2 is an enlarged view of the operation panel 10. The operation panel 10 includes a button unit 11 on which control buttons are arranged, and a display unit 16. The button unit 11 includes an up button 12 for raising the height of the table 300, a down button 13 for lowering the height of the table 300, and the like.

When the operator 401 wishes to roughly adjust the height of the table 300, the operator 401 presses the up button 12 or the down button 13 for a long time. For example, when the operator wishes to continuously raise the height of the table 300, the operator 401 presses the up button 12 for a long time. When the up button 12 is pressed and held, the height of the table 300 is continuously raised for as long as the up button 12 is pressed and held by the operator 401. On the other hand, when the operator wishes to continuously lower the height of the table 300, the operator 401 presses the down button 13 for a long time. When the down button 13 is pressed and held, the height of the table 300 is continuously lowered for as long as the down button 13 is pressed and held by the operator 401.

Figure 3:
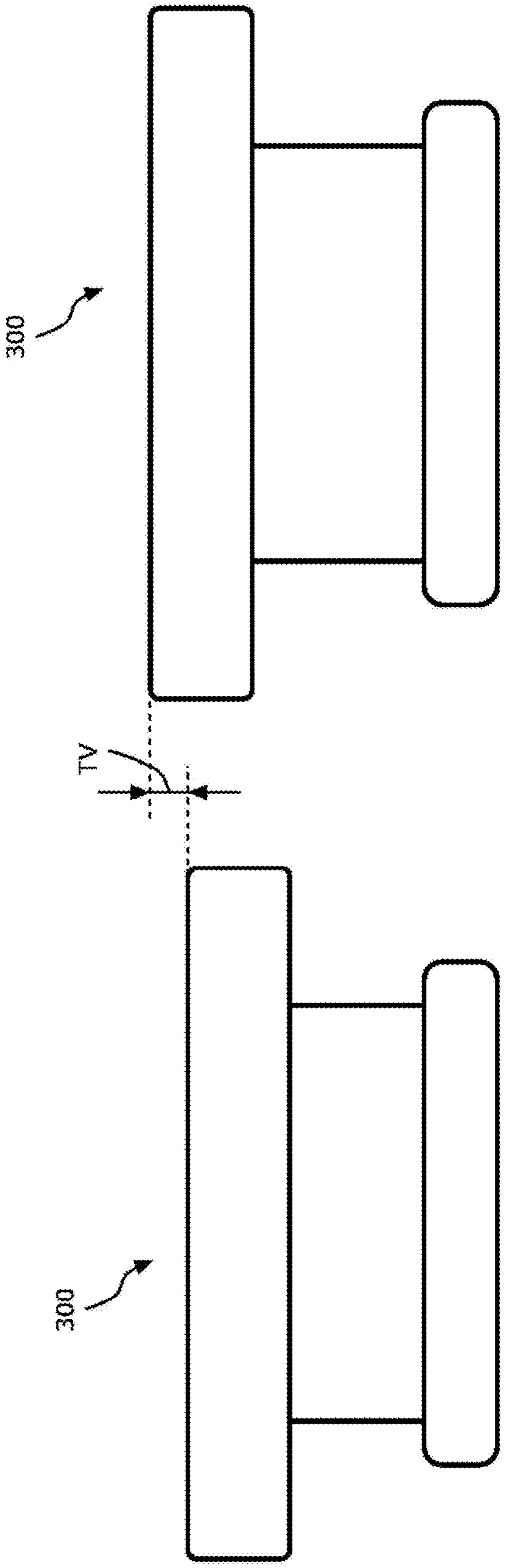
FIG. 3 is an explanatory diagram for a case where an up button 12 is tapped.

Furthermore, when the operator 401 wishes to fine adjust the height of the table 300, the operator 401 performs an operation of pressing the up button 12 or the down button 13 and immediately releasing the button 12 or 13 (hereinafter referred to as a "tap operation"). FIG. 3 is an explanatory diagram for a case where an up button 12 is tapped. The table 300 depicted on the left half of FIG. 3 depicts the height of the table before the up button 12 is tapped, and the table 300 depicted on the right half of FIG. 3 depicts the height of the table after the up button 12 is tapped. The table 300 is set so that one tap operation increases the value by the target change amount TV. In FIG. 3, the target change amount TV is exaggerated to facilitate understanding, but in reality, the target change amount TV is a value of approximately TV=0.1 (mm) to 0.5 (mm). Therefore, the operator 401 can precisely control the amount of rise in the height of the table 300 by performing a tapping operation on the up button 12.

Figure 4:
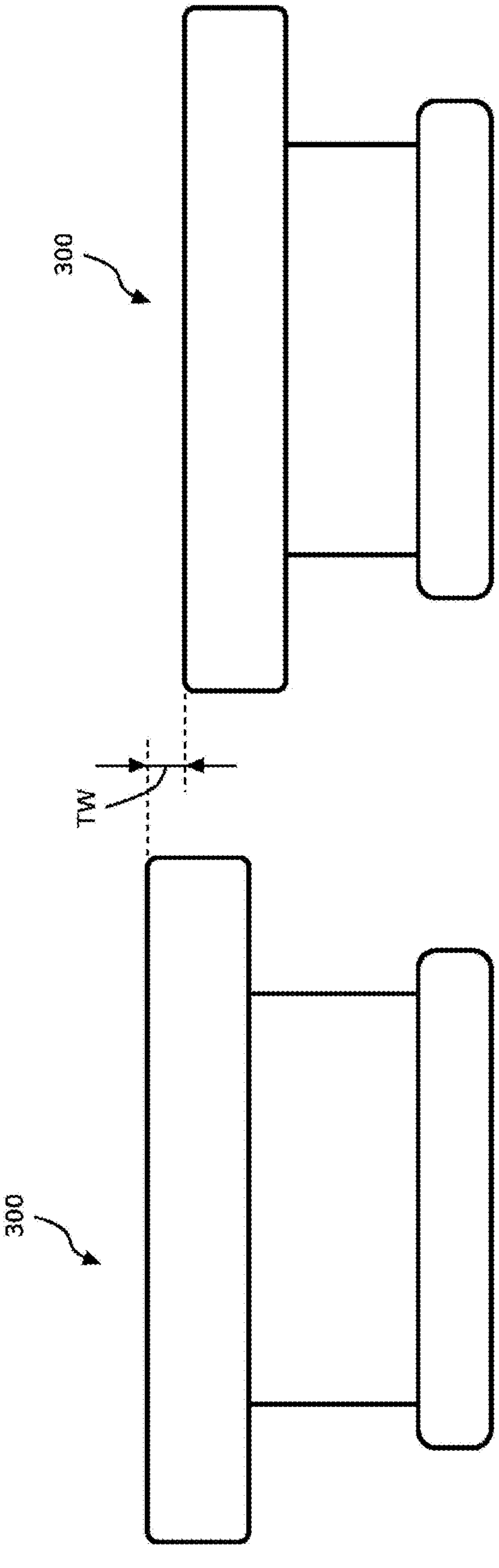
FIG. 4 is an explanatory diagram for a case where a down button 13 is tapped.

On the other hand, FIG. 4 is an explanatory diagram of a case where the down button 13 is tapped. The table 300 depicted on the left half of FIG. 4 depicts the height of the table before the down button 13 is tapped, and the table 300 depicted in the right half of FIG. 4 depicts the height of the table after the down button 13 is tapped. The table 300 moves down by the target change amount TW as a result of one tap operation. In FIG. 4, the target change amount TW is exaggerated to facilitate understanding, but in reality, the target change amount TW is a value of approximately 0.1 (mm) to 0.5 (mm). Therefore, by performing a tap operation on the down button 13, the descending amount can be precisely controlled so that the height of the table 300 is lowered.

The display unit 16 of the operation panel 10 includes a display region 17. The display region 17 is a region where the current height of the table 300 is displayed.

Therefore, the operator 401 can adjust the height of the table 300 by tapping the up button 12 or the down button 13 while checking the current height of the table 300 on the display unit 16. Next, a control device that controls the height of the table in response to an operation from the operation panel 10 will be described.

Figure 5:
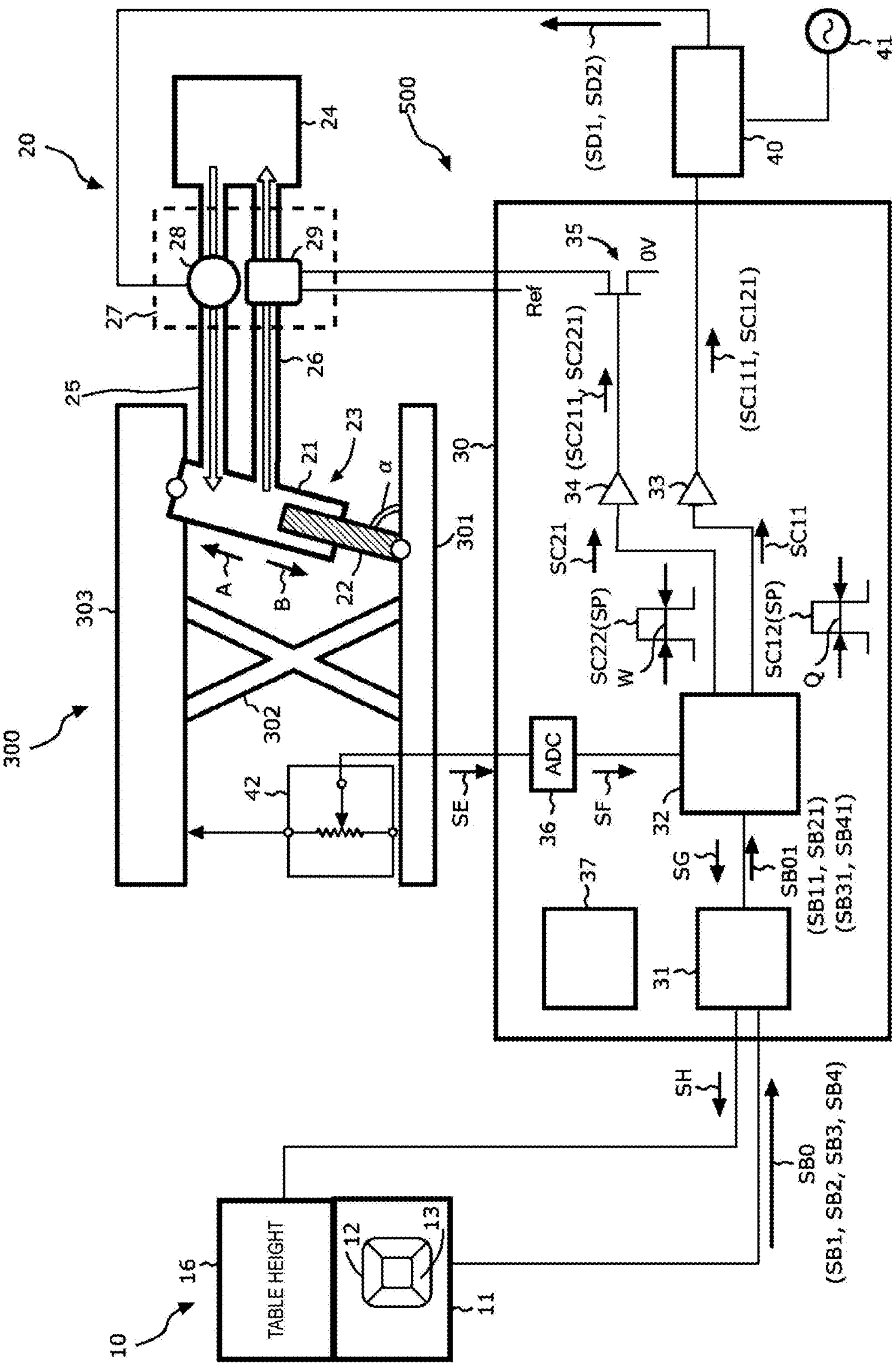
FIG. 5 is a block diagram of a table and a table control device.

FIG. 5 is a block diagram of the table and the table control device. The table 300 includes a base part 301, legs 302, and a subject support unit 303. The subject support unit 303 supports a subject (such as a patient or the like). The legs 302 connect the base part 301 to the subject support unit 303. The legs 302 are configured to be extendable and contractable in the height direction of the table 300, and the legs 302 extend and contract in accordance with changes in the height of the table 300. In addition, the table 300 has a table control device 500 that controls the height of the table. The table control device 500 will now be described.

The table control device 500 has a hydraulic device 20 for adjusting the height of the subject support unit 303. The hydraulic device 20 includes a unit 23 which has a cylinder 21 and a piston 22, an oil tank 24, a supply pipe 25 that supplies oil in the oil tank 24 to the cylinder 21, a discharge pipe 26 that discharges the oil in the cylinder 21 to the oil tank 24, and an oil amount adjustment unit 27 that adjusts the amount of oil in the cylinder 21.

Although the hydraulic device 20 is attached to the table 300, in FIG. 5, some of the structural elements of the hydraulic device 20 are depicted protruding from the table 300 in order to make the structural element of the hydraulic device 20 easier to understand. Furthermore, in FIG. 5, the unit 23 including the cylinder 21 and the piston 22 is depicted enlarged in order to facilitate understanding of the structure of the unit 23. The structural elements of the hydraulic device 20 will now be described in order.

The unit 23 is configured such that at least a portion of the piston 22 is disposed within the cylinder 21, and one of either the cylinder 21 or the piston 22 moves relative to the other by adjusting the amount of oil in the cylinder 21. For example, the piston 22 may be configured to be able to reciprocate relative to the cylinder 21, the cylinder 21 may be configured to be able to reciprocate relative to the piston 22, or the cylinder 21 and the piston 22 may be configured to be able to reciprocate relative to each other. In addition, the cylinder 21 and the piston 22 may be configured so that the angle $\alpha$ between the cylinder 21 and the piston 22 is maintained at a fixed angle while the height of the subject support unit 303 is being adjusted, or the angle $\alpha$ may be configured so that the angle is continuously changed. The height of the subject support unit 303 can be adjusted by the aforementioned configuration of the cylinder 21 and the piston 22. A method for adjusting the height of the subject support unit 303 in the present embodiment will be described below in detail.

Furthermore, the hydraulic device 20 also includes an oil tank 24, a supply pipe 25 that supplies oil in the oil tank 24 to the cylinder 21, a discharge pipe 26 that discharges the oil in the cylinder 21 to the oil tank 24, and an oil amount adjustment unit 27 that adjusts the amount of oil in the cylinder 21.

The oil amount adjustment unit 27 includes a pump 28 and a valve 29. The pump 28 is configured to supply oil from the oil tank 24 to the cylinder 21 through the supply pipe 25. The valve 29 is configured to drain oil from the cylinder 21 through the discharge pipe 26 back to the oil tank 24. In the present embodiment, oil is used as the working fluid of the hydraulic device 20, but a fluid other than oil can be used as the working fluid.

Furthermore, the table control device 500 also includes a control board 30 and an inverter 40. The control board 30 and the inverter 40 are configured to control the operation of the hydraulic device 20. The control board 30 and the inverter 40 will be described below.

Based on an operation signal for raising and lowering the subject support unit 303 by the target change amount, the control board 30 generates a control signal including a control pulse width corresponding to the target change amount so that the subject support unit 303 is raised and lowered by the target change amount. The control board 30 includes a storage device 37. The storage device 37 includes one or more storage media that store programs, instructions, and the like to be executed by the processor. The storage medium can be, for example, one or more non-transitory, computer-readable storage media. The storage media may include, for example, hard disk drives, floppy disk drives, compact disc rewritable (CD-R/W) drives, digital versatile disk (DVD) drives, flash drives, and/or solid state recording drives. Although FIG. 5 depicts the control board 30 as including one storage device 37, the control board 30 may include a plurality of storage devices 37. Furthermore, the plurality of storage devices 37 may be provided on the control board 30, or may be provided distributed between the control board 30 and other structural elements other than the control board 30.

The control board 30 includes a converter 31. The converter 31 is connected to the operation panel 10. The converter 31 receives an operation signal SB0 input by the operator 401 operating the button 12 or 13. For example, when the operator 401 presses the up button 12 for a long time, the operation signal SB0 represents an operation signal SB1 for continuously raising the height of the table 300. On the other hand, when the operator 401 taps the up button 12, the operation signal SB0 represents a signal SB2 for raising the table 300 by a prescribed target change amount TV (see FIG. 3). With reference to FIG. 3, the target change amount TV is exaggerated to facilitate understanding, but in reality, the target change amount TV is a value of approximately TV=0.1 (mm) to 0.5 (mm).

Furthermore, when the operator 401 executes an operation of long pressing the down button 13, the operation signal SB0 represents a signal SB3 for continuously lowering the height of the table 300. On the other hand, when the operator 401 taps the down button 13, the operation signal SB0 represents a signal SB4 for lowering the height of the table 300 by a prescribed target change amount TW (see FIG. 4). With reference to FIG. 4, the target change amount TW is exaggerated to facilitate understanding, but in reality, the target change amount TW is a value of approximately TW=0.1 (mm) to 0.5 (mm).

The target change amount TV when raising the height of the table 300 and the target change amount TW when lowering the height of the table 300 are the same (in other words, TV=TW). However, TV≠TW is also possible.

When the converter 31 receives an operation signal SB0 from button 12 or 13, the converter converts the signal to the voltage of the operation signal SB0 and outputs a voltage-converted signal SB01 (SB11, SB21, SB31, SB41). The voltage-converted signal SB11 is a signal including a command to continuously raise the height of the table 300, and the voltage-converted signal SB21 is a signal including a command to raise the height of the table 300 by the target change amount TV. Furthermore, the voltage-converted signal SB31 is a signal including a command to continuously lower the height of the table 300, and the voltage-converted signal SB41 is a signal including a command to lower the height of the table 300 by the target change amount TW.

Furthermore, the control board 30 also includes a processor 32. The processor 32 generates a control signal for controlling the oil amount adjustment unit 27 of the hydraulic device 20 based on the signal SB01 received from the converter 31. Although FIG. 5 depicts the control board 30 as including one processor 32, the control board 30 may include a plurality of processors 32. Furthermore, the plurality of processors 32 may be provided on the control board 30, or may be provided distributed between the control board 30 and other structural elements other than the control board 30.

When the processor 32 receives a signal SB11 including a command to continuously raise the height of the table 300 from the converter 31, the processor generates a control signal SC11 to continuously supply oil to the cylinder 21. The control signal SC 11 is supplied to the buffer 33, and after a prescribed process is performed in the buffer 33, the control signal SC 111 is supplied to the inverter 40. When the inverter 40 receives the control signal SC111, the inverter supplies an AC signal SD1 from the AC source 41 to the pump 28. The pump 28 continuously supplies oil from the oil tank 24 to the cylinder 21 based on the AC signal SD1. Therefore, the cylinder 21 moves in the direction of arrow A relative to the piston 22 so that the subject support unit 303 rises continuously. In this manner, the subject support unit 303 constitutes a movable body that moves in response to the relative movement of the cylinder 21 and the piston 22.

In addition, when the processor 32 receives a signal SB21 including a command to raise the height of the table 300 by the target change amount TV from the converter 31, the processor generates a control signal SC12 to supply an amount of oil corresponding to the target change amount TV to the cylinder 21. This control signal SC12 is a pulse signal SP, and the pulse width Q of the control signal SC12 expresses the time corresponding to the target change amount TV. For example, the pulse width Q=330 ms. The control signal SC12 is supplied to the buffer 33, and after a prescribed process is performed in the buffer 33, the control signal SC121 is supplied to the inverter 40. When the inverter 40 receives the control signal SC121, the inverter supplies the AC signal SD2 from the AC source 41 to the pump 28 for a period of time corresponding to the pulse width Q=330 ms. Based on the AC signal SD2, the pump 28 supplies oil from the oil tank 24 to the cylinder 21 in an amount corresponding to the pulse width Q(=330 ms). Therefore, the pump 28 can adjust the amount of oil contained in the cylinder 21 based on the pulse width Q(=330 ms). As a result, the cylinder 21 is fine adjusted in the direction of arrow A, and the subject support unit 303 is raised by the target change amount TV.

Furthermore, when the processor 32 receives a signal SB31 including a command to continuously lower the height of the table 300 from the converter 31, the processor generates a control signal SC21 to continuously supply oil to the cylinder 21. The control signal SC21 is supplied to the buffer 34, and after a prescribed process is performed in the buffer 34, the control signal SC211 is supplied to the TFT 35. When the control signal SC211 is supplied, the TFT 35 is turned on. When the TFT 35 is turned on, a prescribed reference voltage Ref is applied to the valve 29, and the valve 29 opens. At this time, the TFT 35 maintains the ON state while the operator 401 is pressing the down button 13. Therefore, the valve 29 discharges oil in the cylinder 21 into the oil tank 24. Therefore, the cylinder 21 moves in the direction of arrow B, and as a result, the subject support unit 303 moves down continuously.

In addition, when the processor 32 receives a signal SB41 including a command to lower the height of the table 300 by the target change amount TW from the converter 31, the processor generates a control signal SC22 to discharge an amount of oil corresponding to the target change amount TW from the cylinder 21. The control signal SC22 is a pulse signal SP, and the pulse width W of the control signal SC22 represents a time period corresponding to the target change amount TW. For example, the pulse width W=330 ms. The control signal SC12 is supplied to the buffer 33, and after a prescribed process is performed in the buffer 33, the control signal SC221 is supplied to the TFT 35. When the control signal SC221 is supplied, the TFT 35 is turned on. When the TFT 35 is turned on, a prescribed reference voltage Ref is applied to the valve 29, and the valve 29 opens. At this time, the TFT 35 maintains the ON state for a period of time corresponding to the pulse width W=330 ms. Therefore, an amount of oil corresponding to the pulse width W is discharged from the cylinder 21 to the oil tank 24, and the amount of oil in the cylinder 21 is adjusted. Therefore, the cylinder 21 is fine adjusted in the direction of arrow B, and as a result, the subject support unit 303 is lowered by the target change amount TW.

Furthermore, the table control device 500 also includes a potentiometer 42. The potentiometer 42 outputs an analog signal SE that indicates a voltage corresponding to the raising or lowering of the subject support unit 303 by adjusting the amount of oil in the cylinder 21. The ADC 36 converts the analog signal SE to a digital signal SF which is then output to the processor 32. The processor 32 calculates the current height of the table 300 according to the button operation of the operator 401 based on the digital signal SF received from the ADC 36. The processor 32 outputs a digital signal SG representing the current height of the table 300 to the converter 31. The converter 31 adjusts the voltage of the digital signal SG received from the processor 32, and transmits the voltage-adjusted signal SH to the display unit 16. The signal SH contains information representative of the current height of the table 300. Therefore, the display unit 16 displays the current height of the table 300 based on the signal SH. Therefore, the operator 401 can recognize the current height of the table 300 in real time by looking at the display unit 16.

The table control device 500 is configured as described above. Next, an example will be described of a procedure in which the operator 401 adjusts the height of the table 300 while operating the button unit 11 in the present embodiment when imaging a subject.

An operator 401 lies the subject 400 on the table 300 (see FIG. 1), and then adjusts the height of the table 300. First, the operator 401 presses the up button 12 for a long time to adjust the table 300 to a height suitable for imaging. As long as the operator 401 presses the up button 12, the table 300 continues to rise until approaching the desired height of the table 300. Furthermore, if the operator 401 raises the height of the table 300 too high, the operator presses the down button 13 for a long time. As long as the down button 13 is pressed, the table 300 continues to lower, allowing the operator 401 to quickly lower the height of the table 300 to be near the desired position.

After roughly positioning the height of the table 300, the operator 401 fine adjusts the height of the table 300. Consider the case where the operator 401 wishes to fine adjust the table 300 down from the current height.

In the following, in order to clarify the difference between the present embodiment and the conventional method, first, a method for fine adjusting the height of the table 300 in using the conventional method will be described. Furthermore, after describing the conventional method, the specific method of the present embodiment will be described.

Figure 6:
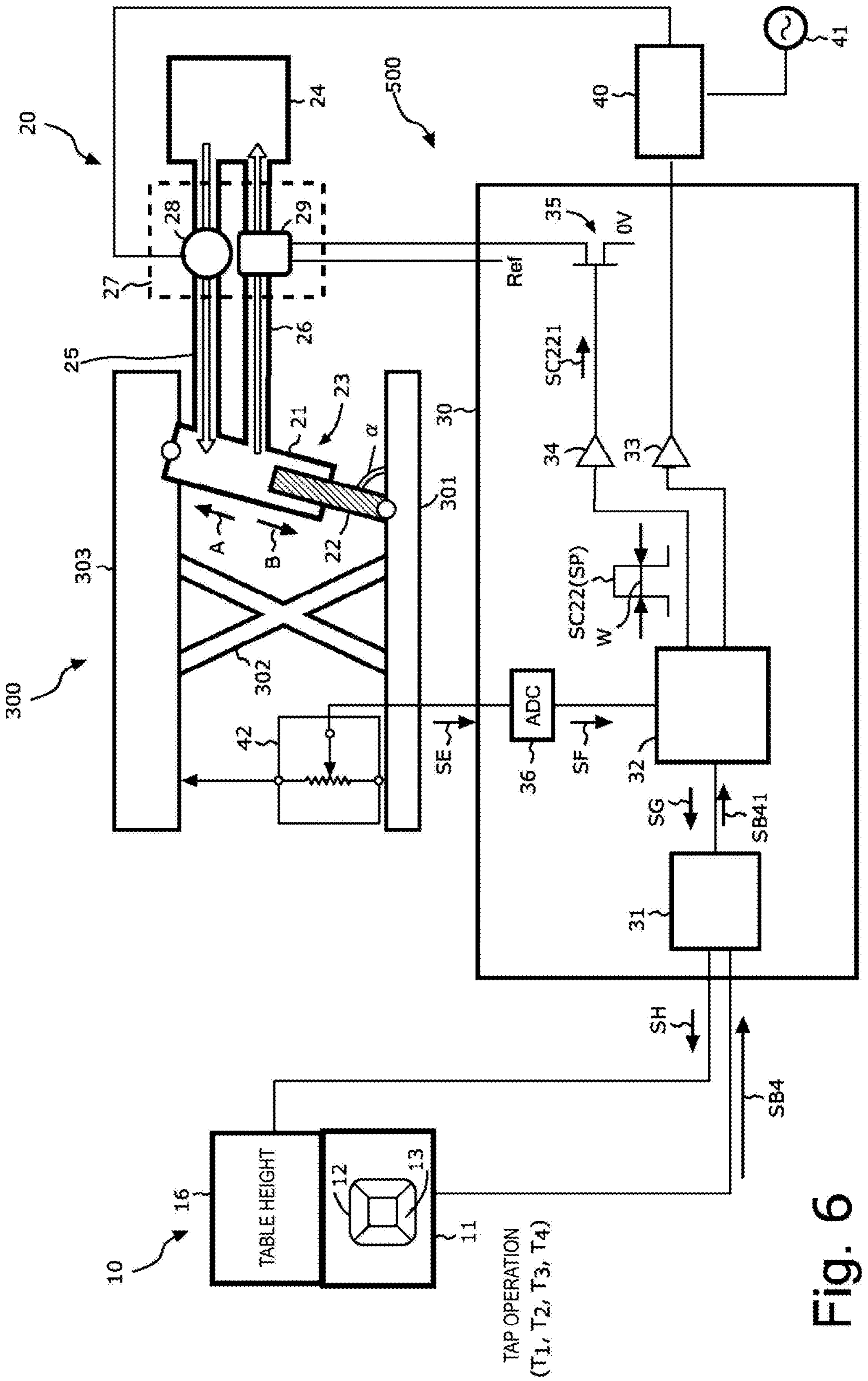
FIG. 6 is a block diagram of a table and a table control device.
Figure 7:
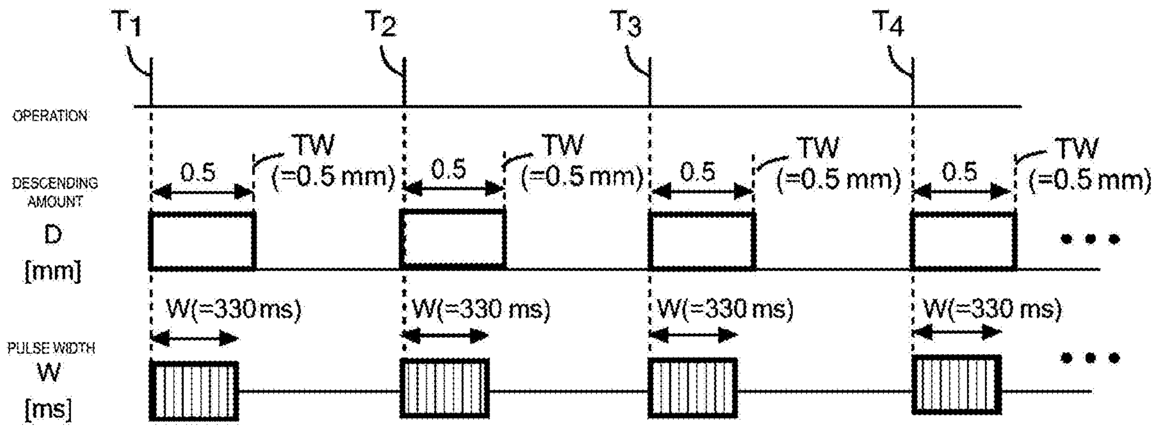
FIG. 7 is a diagram depicting a pulse width W and a descending amount D of the table 300 corresponding to a tap operation by an operator 401.

In the following, a conventional method for fine adjusting a table will be described by taking an example in which an operator 401 fine adjusts the table by performing a tapping operation on the down button 13 on the operation panel 10. Conventional fine adjustment will be described with reference to FIGS. 6 and 7. Note that FIG. 6 depicts a block diagram of FIG. 5, but FIG. 5 also includes reference numbers that are not used in the following description of the fine adjustment of the table. Therefore, FIG. 6 is prepared by deleting unnecessary reference numerals from FIG. 5 in order to facilitate understanding of the drawings. FIG. 7 depicts a schematic diagram of the pulse width W and the descending amount D of the table 300 corresponding to the tapping operation of the operator 401.

First, the operator 401 performs a tap operation $T_1$ on the down button 13 so that the table 300 moves down by a prescribed target change amount. The tap operation $T_1$ is depicted in FIG. 7. When a tap operation $T_1$ is performed, as depicted in FIG. 6, an operation signal SB4 for lowering the table 300 by the target change amount TW (see FIG. 4) is output from the operation panel 10 and input to the converter 31. Upon receiving the operation signal SB4, the converter 31 converts the voltage of the operation signal SB4 and outputs a voltage-converted signal SB41. The voltage-converted signal SB41 is a signal including a command for lowering the height of the table 300 by the target change amount TW.

When the processor 32 receives a signal SB41 including a command to lower the height of the table 300 by the target change amount TW from the converter 31, the processor generates a control signal SC22 to discharge an amount of oil corresponding to the target change amount TW from the cylinder 21. This control signal SC22 is a pulse signal SP, and the pulse width W of the control signal SC22 is a fixed value. FIG. 7 depicts an example where the pulse width W is 330 ms, but W may be a value other than 330 ms. The control signal SC22 including the pulse width W(=330 ms) is supplied to a buffer 34, and after a prescribed process is performed in the buffer 34, a control signal SC221 is supplied to a TFT 35. When the control signal SC221 is supplied, the TFT 35 is turned on. When the TFT 35 is turned on, a prescribed reference voltage Ref is applied to the valve 29, and the valve 29 opens. At this time, the TFT 35 maintains the ON state for a period of time corresponding to the pulse width W(=330 ms). Therefore, an amount of oil corresponding to the pulse width W is discharged from the cylinder 21 to the oil tank 24. Therefore, the cylinder 21 is fine adjusted in the direction of arrow B, and as a result, the table 300 is lowered. FIG. 7 depicts the descending amount D of the table 300 corresponding to the operation $T_1$. Here, the target change amount TW of the descending amount D of the table 300 is 0.5 mm, and the state in which the descending amount D coincides with the target change amount TW by the operation $T_1$ is depicted.

Similarly, the table 300 can be lowered by 0.5 mm each time a tap operation $T_2$, $T_3$, $T_4$ . . . is performed.

Figure 8:
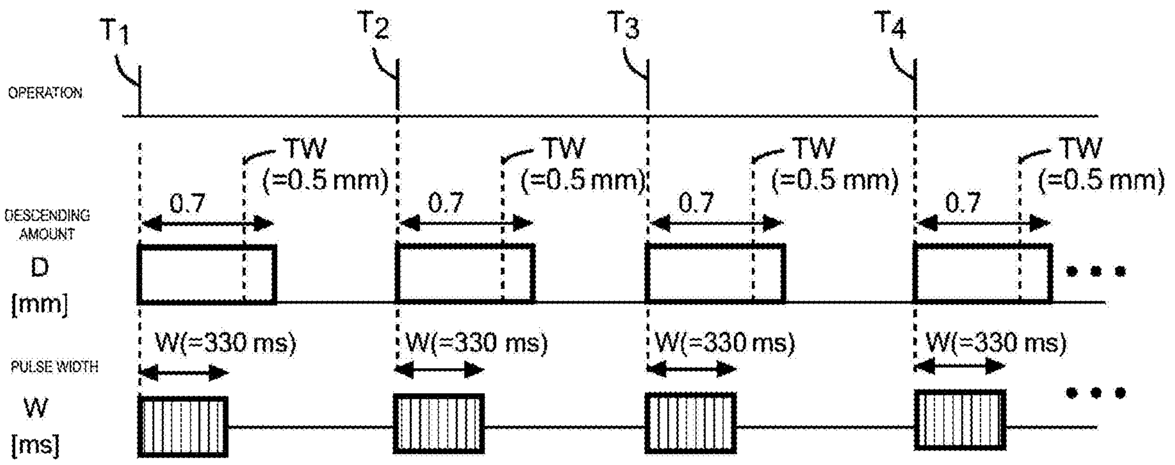
FIG. 8 is an explanatory diagram for a case where the descending amount D of the table 300 deviates from the target change amount TW.

However, depending on the environment in which the gantry is used, the descending amount D of the table 300 may deviate from the target change amount TW (see FIG. 8).

FIG. 8 is an explanatory diagram of a case where the descending amount D of the table 300 deviates from the target change amount TW. In FIG. 8, when the operator 401 taps the down button 13 (an operation to move the table 300 down by the target change amount TW) $T_1$, the processor 32 outputs a control signal with a pulse width W(=330 ms) as described in FIG. 7. The pulse width W=330 ms represents a pulse width that ideally lowers the table 300 by a target change amount TW (for example, 0.5 mm).

However, in FIG. 8, the table 300 is lowered by an amount (for example, 0.7 mm) that deviates from the target change amount TW. In this manner, the descending amount D of the table 300 may not coincide with the target change amount TW due to the influence of the environment in which the table is used. Similarly, the operator 401 continues operations $T_2$, $T_3$, $T_4$ . . . , but the descending amount D does not match the target change amount TW. Therefore, operations $T_1$ to $T_4$ should ideally be operations for lowering the height of table 300 by the target change amount TW. However, in reality, even if operations $T_1$ to $T_4$ are executed, the descending amount D of table 300 deviates from the target change amount TW. This causes a problem in that time is required for the operator 401 to align table 300 to the desired height, which increases the workload of the operator 401.

Therefore, the present inventors conducted intensive research and conceived of a method for making the deviation DM between the actual descending amount D of table 300 and the target change amount TW to be zero (or approaching zero) as quickly as possible, even if the actual descending amount D of table 300 deviates from the target change amount TW during fine adjustment of the height of the table. A method for fine adjusting the height of the table 300 according to the present embodiment will be described below.

Figure 9:
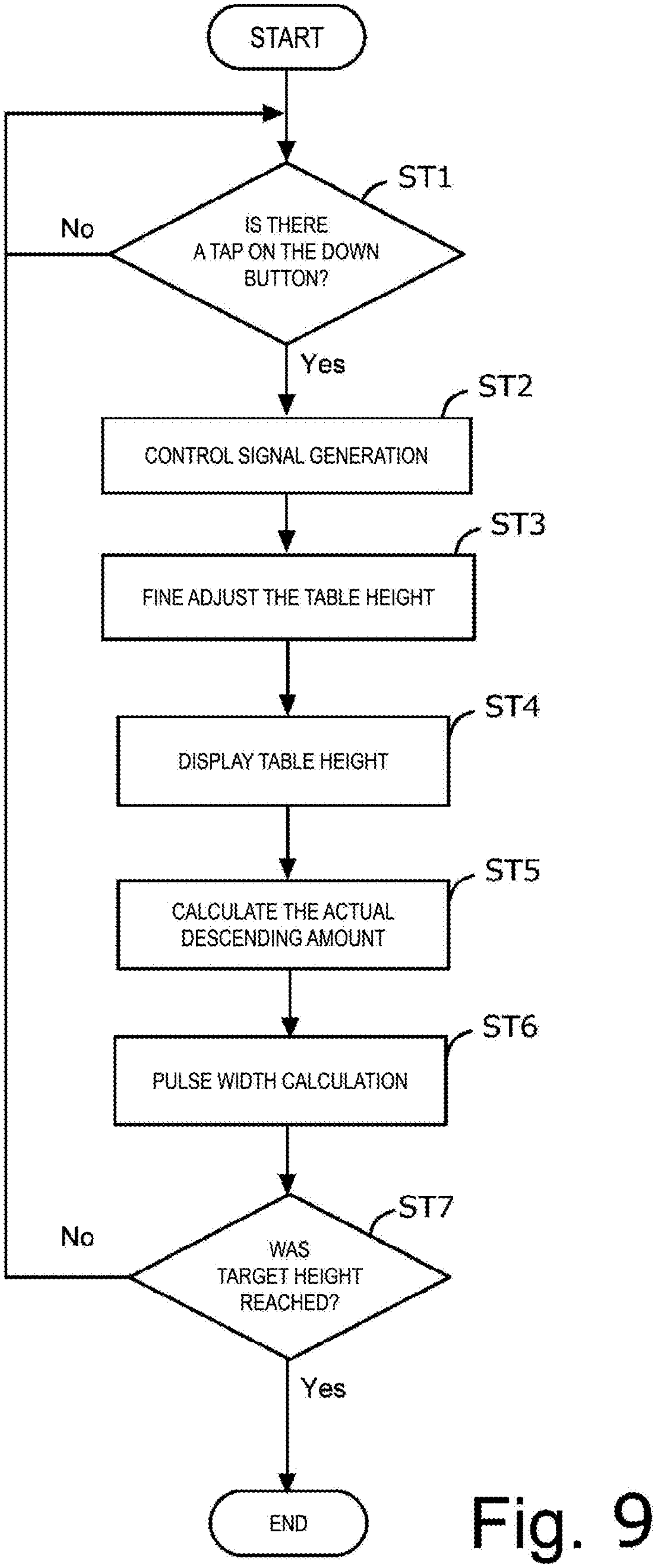
FIG. 9 is a diagram depicting an operation flow of the table 300 when fine adjusting the height of the table 300 according to the present embodiment.
Figure 10:
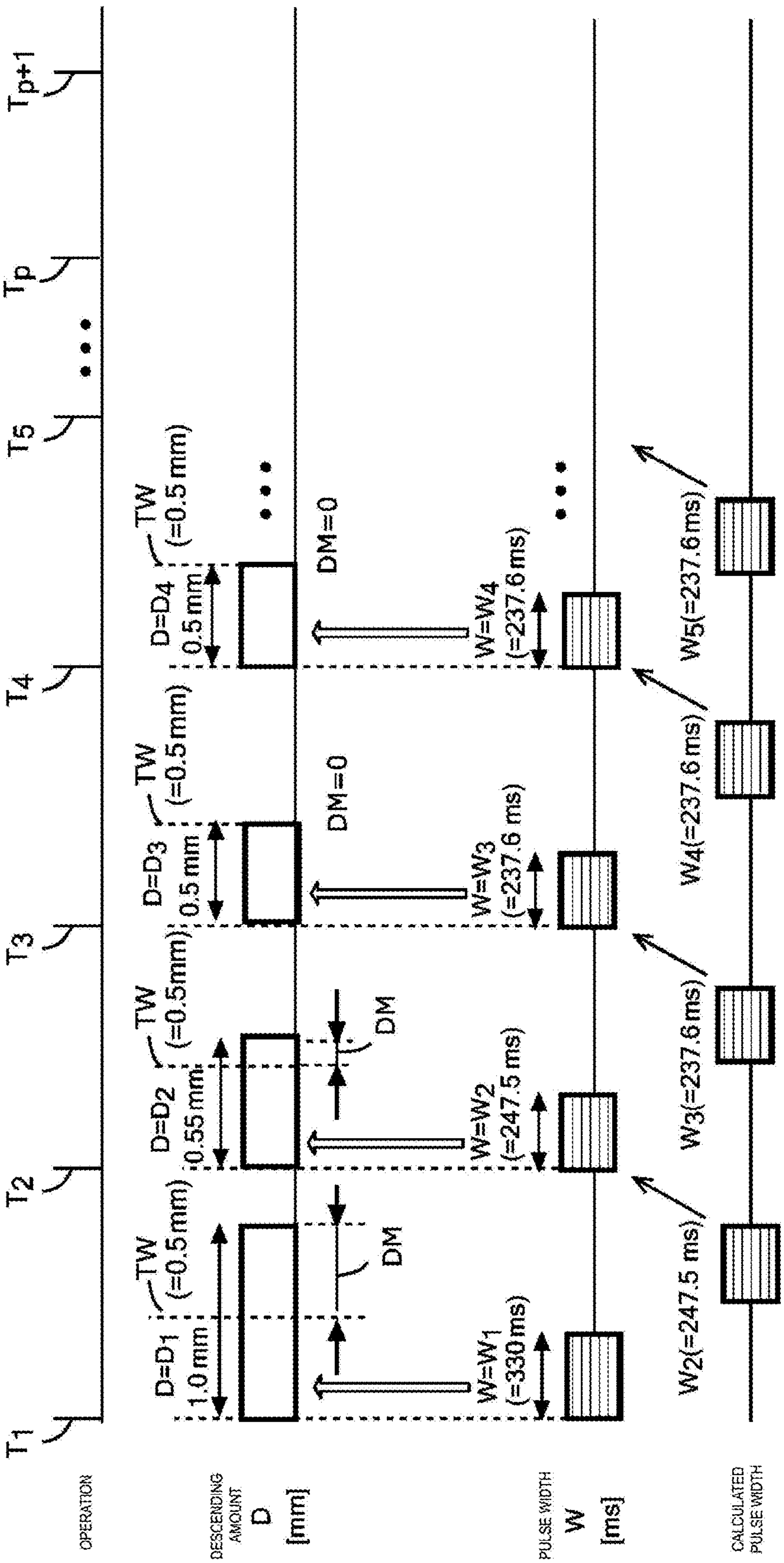
FIG. 10 is a diagram depicting a pulse width W and a descending amount D of the table 300 corresponding to an operation of the operator 401.

The method of fine adjusting the table of the present embodiment will be described with reference to FIG. 9. FIG. 9 is a diagram depicting an operation flow of the table 300 when fine adjusting the height of the table 300 according to the present embodiment. Note that FIG. 9 will be described with reference to FIGS. 6 and 10 as necessary. FIG. 6 is a block diagram of the table control device 500, and FIG. 10 depicts the pulse width W and the descending amount D of the table 300 corresponding to an operation by the operator 401.

In step ST1, the processor 32 waits for a tap operation $T_1$ (see FIG. 10) of the down button 13. When the operator 401 taps the down button 13 ($T_1$), the process proceeds to step ST2.

In step ST2, as depicted in FIG. 6, an operation signal SB4 for lowering the height of the table 300 by the target change amount TW is output from the operation panel 10 and input to the converter 31. Here, the target change amount TW is described as TW=0.5 mm, but TW can be set to a value smaller than 0.5 mm, for example, a value smaller than 0.1 mm. Upon receiving the operation signal SB4, the converter 31 converts the voltage of the operation signal SB4 and outputs a voltage-converted signal SB41. The voltage-converted signal SB41 is a signal including a command for lowering the height of the table 300 by the target change amount TW. The processor 32 receives a signal SB41 including a command to lower the height of the table 300 by a target change amount TW from the converter 31, and generates a control signal SC22 including a pulse width $W=W_1$ based on the signal SB41. The control signal SC22 is a pulse signal SP. The pulse width $W_1$ corresponding to operation $T_1$ is $W_1$=330 ms, as depicted in FIG. 10. After the control signal SC22 is generated, the process proceeds to step ST3.

In step ST3, the height of the table 300 is fine adjusted based on the control signal SC22. Specifically, the height of the table 300 is fine adjusted as described below. As depicted in FIG. 6, the control signal SC22 is supplied to a buffer 34, and after a prescribed process is performed in the buffer 34, a control signal SC221 is supplied to the TFT 35. When the control signal SC221 is supplied, the TFT 35 is turned on. When the TFT 35 is turned on, a prescribed reference voltage Ref is applied to the valve 29, and the valve 29 opens. At this time, the TFT 35 maintains the ON state for a period of time corresponding to the pulse width $W_1$ (=330 ms). Therefore, an amount of oil corresponding to the pulse width $W_1$ is discharged from the cylinder 21 to the oil tank 24. Therefore, the cylinder 21 moves in the direction of arrow B, and the subject support unit 303 moves down, so that the height of the table 300 is fine adjusted.

In step ST4, the height of the table 300 is displayed. Specifically, the height of the table 300 is displayed as described below. The potentiometer 42 outputs an analog signal SE that indicates a voltage corresponding to lowering of the subject support unit 303 by adjusting the amount of oil in the cylinder 21. The ADC 36 converts the analog signal SE to a digital signal SF which is then output to the processor 32. The processor 32 calculates the current height of the table 300 corresponding to operation $T_1$ by the operator 401 based on the digital signal SF received from the ADC 36. The processor 32 outputs a digital signal SG representing the current height of the table 300 to the converter 31. The converter 31 adjusts the voltage of the digital signal SG received from the processor 32, and transmits the voltage-adjusted signal SH to the display unit 16. The signal SH contains information representative of the current height of the table 300. Therefore, the display unit 16 can display the current height of the table 300 based on the signal SH. Therefore, the operator 401 can recognize the current height of the table 300 in real time by looking at the display unit 16.

In step ST5, the processor 32 calculates the actual descending amount D of the table 300 based on the digital signal SE received from the ADC 36. FIG. 10 depicts a descending amount $D=D_1$ of the table 300 corresponding to the operation $T_1$. Here, $D_1$=1.0 mm. After the descending amount $D=D_1$(=1.0 mm) is calculated, the process proceeds to step ST6.

In step ST6, the processor 32 uses the pulse width $W_1$ used in the tap operation $T_1$ to calculate the pulse width $W_2$ to be used when lowering the table in the next tap operation $T_2$. This pulse width $W_2$ is calculated using Formula (1) below.

$$W_2 = W_1 - W_1 * K * DM \tag{1}$$

$W_2$: pulse width used in the next operation $T_2$ $W_1$: pulse width used in operation $T_1$ K: Gain DM: Deviation calculated in operation $T_1$ Therefore, the pulse width $W_2$ is clearly a value that depends on the gain K. The gain K is a value that is determined based on the deviation DM.

Figure 11:
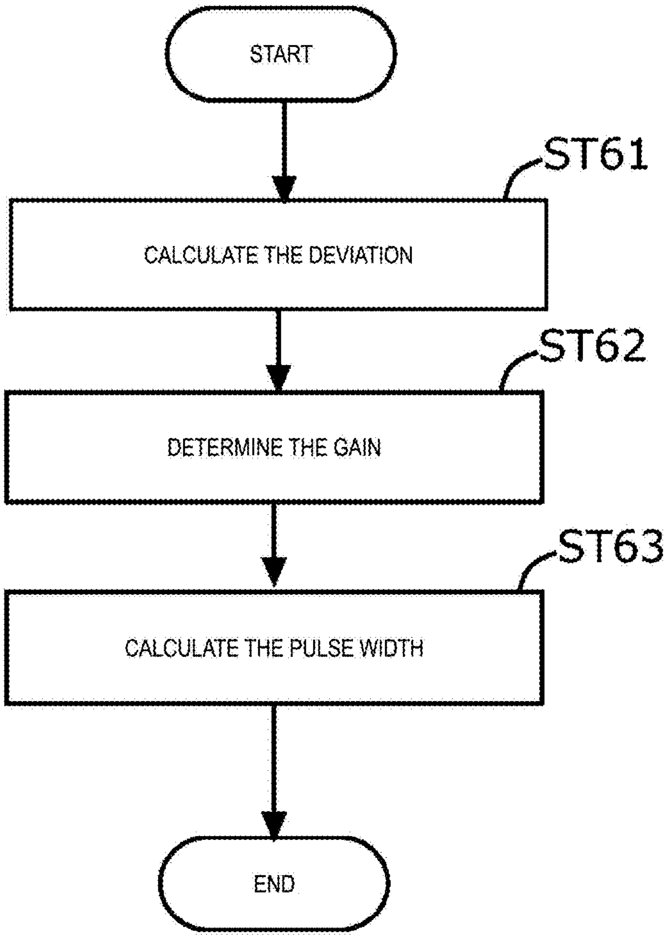
FIG. 11 is a flow chart of a method for calculating the pulse width $W_2$ in step ST6.

A method for calculating the pulse width $W_2$ using Formula (1) will be described below with reference to FIG. 11. FIG. 11 is a flow chart of a method for calculating the pulse width $W_2$ in step ST6. In step ST61, the processor 32 calculates the deviation DM, which is the difference between the descending amount D calculated in step ST5 and the target change amount TW. The deviation DM is expressed by the following formula (2).

$$DM = D_1 - TW \tag{2}$$

$D_1$: descending amount when the operation $T_1$ is executed

TW: target change amount.

In the present embodiment, the target change amount TW is 0.5 mm. Furthermore, the descending amount $D_1$ from operation $T_1$ is $D_1$=1.0 mm. Therefore, the deviation DM is expressed by the following Formula (3).

$$DM = D_1 - TW = 1.0 - 0.5 = 0.5 \text{ (mm)} \tag{3}$$

After calculating the deviation DM, the process proceeds to step ST62. In step ST62, the processor 32 determines the gain value K based on the deviation DM. In the present embodiment, the gain K is determined based on the following three conditions (4) to (6).

$$DM > 0.15: K = 0.5 \tag{4}$$

$$0.15 \geqq DM \geqq -0.05: K = 0.8 \tag{5}$$

$$-0.05 > DM: K = 1.8 \tag{6}$$

In other words, if DM>0.15, the processor 32 determines the gain K to be K=0.5; if 0.15≥DM≥−0.05, the processor determines the gain K to be K=0.8, and if −0.05>DM, the processor determines the gain K to be K=1.8. Here, DM is calculated as DM=0.5 mm as depicted in Formula (3). Therefore, since DM satisfies condition (4), processor 32 determines that the gain K is K=0.5. In the present embodiment, the gain K is determined based on three conditions, but the gain K may be determined based on two conditions, or the gain K may be determined based on four or more conditions. After the gain K is determined, the process proceeds to step ST63.

In step ST63, the pulse width $W_2$ is calculated based on Formula (1). It can be seen from FIG. 10 that $W_1$=330 ms. Furthermore, the gain K is determined to be 0.5 in step ST62. Furthermore, the deviation DM is DM=0.5 mm according to formula (3). Therefore, by substituting these values into Formula (1), the pulse width $W_2$ can be calculated as described below.

$$W_2 = W_1 - W_1 * K * DM = 330 \text{ ms} - 330 \text{ ms} * 0.5 * 0.5 = 247.5 \text{ ms} \quad (7)$$

Therefore, in the operation $T_1$, pulse width $W_1$=330 ms was used, but in the process of step ST6, the pulse width $W_2$ corresponding to the next operation $T_2$ is calculated as $W_{2=247.5}$ ms. FIG. 10 depicts the calculated pulse width $W_2$ (=247.5 mm). Once the pulse width $W_2$ has been calculated, the process proceeds to step ST7.

In step ST7, the processor 32 determines if the table 300 has reached the target height. When the table 300 reaches the target height, the flow ends. On the other hand, if the table 300 has not reached the target height, the process returns to step ST1. Here, it is assumed that the table 300 has not reached the target height. Therefore, the process returns to step ST1.

In step ST1, the processor 32 waits for a tap operation $T_2$ (see FIG. 10) of the down button 13. When the operator 401 taps the down button 13 in a tap operation $T_2$, the process proceeds to step ST2.

In step ST2, as depicted in FIG. 6, an operation signal SB4 for lowering the height of the table 300 by the target change amount TW is output from the operation panel 10 and input to the converter 31. Upon receiving the operation signal SB4, the converter 31 converts the voltage of the operation signal SB4 and outputs a voltage-converted signal SB41. The processor 32 generates a control signal SC22 including a pulse width W=$W_2$ expressed by Formula (7) based on the signal SB41 from the converter 31. FIG. 10 depicts that the pulse width $W_2$ (=247.5 ms) calculated by formula (7) is used as the pulse width W when the tap operation $T_2$ is executed. After the control signal SC22 including the pulse width W(=$W_2$) is generated, the process proceeds to step ST3.

In step ST3, the height of the table 300 is fine adjusted based on the control signal SC22. Specifically, as depicted in FIG. 6, the control signal SC22 is supplied to a buffer 34, and after a prescribed process is performed in the buffer 34, a control signal SC221 is supplied to the TFT 35. When the control signal SC221 is supplied, the TFT 35 is turned on and the valve 29 is opened. At this time, the TFT 35 maintains the ON state for a period of time corresponding to the pulse width $W_2$ (=247.5 ms). Therefore, an amount of oil corresponding to the pulse width $W_2$ is discharged from the cylinder 21 to the oil tank 24. Therefore, the cylinder 21 moves in the direction of arrow B, and the subject support unit 303 moves down, so that the height of the table 300 is fine adjusted.

In step ST4, the display unit 16 displays the current height of the table 300 corresponding to the operation $T_2$, based on the analog signal SE from the potentiometer 42. Once the current height of the table 300 has been displayed, the process proceeds to step ST5.

In step ST5, the processor 32 calculates the actual descending amount D of the table 300 based on the digital signal SE received from the ADC 36. FIG. 10 depicts the descending amount D=$D_2$ of the table 300 corresponding to the operation $T_2$. Here, $D_2$=0.55 mm. After the descending amount D=$D_2$ (=0.55 mm) is calculated, the process proceeds to step ST6.

In step ST6, the processor 32 uses the pulse width $W_2$ used in the tap operation $T_2$ to calculate a pulse width $W_3$ to be used when lowering the table during the next tap operation $T_3$. The pulse width $W_3$ is calculated using Formula (8) below.

$$W_3 = W_2 - W_2 * K * DM \quad (8)$$

$W_3$: pulse width used in the next operation $T_3$,
$W_2$: pulse width used in operation $T_2$,
K: Gain
DM: Deviation calculated in operation $T_2$ Note that when calculating the pulse width $W_3$ using the formula (8), the pulse width $W_3$ can be calculated based on the flow depicted in FIG. 11, similarly to the pulse width $W_2$. Therefore, a method for calculating the pulse width $W_3$ will be described with reference to FIG. 11.

In step ST61, the processor 32 calculates the deviation DM, which is the difference between the descending amount D calculated in step ST5 and the target change amount TW. The deviation DM is expressed by the following Formula (9).

$$DM = D_2 - TW \quad (9)$$

$D_2$: descending amount when operation $T_2$ is executed
TW: target change amount In the present embodiment, the target change amount TW is 0.5 mm. Furthermore, the descending amount $D_2$ caused by operation $T_2$ is $D_2$=0.55 mm. Therefore, the deviation DM is expressed by the following Formula (10).

$$DM = D_2 - TW = 0.55 - 0.5 = 0.05 \text{ (mm)} \quad (10)$$

After calculating the deviation DM, the process proceeds to step ST62. In step ST62, the processor 32 determines the gain value K based on the deviation DM. In the present embodiment, as described above, the gain K is determined based on the following three conditions (4) to (6).

$$DM > 0.15: K = 0.5 \quad (4)$$

$$0.15 \geqq DM \geqq -0.05: K = 0.8 \quad (5)$$

$$-0.05 > DM: K = 1.8 \quad (6)$$

Here, DM is calculated as DM=0.05 mm as depicted in Formula (10). Therefore, since DM satisfies condition (5), the processor 32 determines that the gain K is K=0.8. After the gain K is determined, the process proceeds to step ST63.

In step ST63, the pulse width $W_3$ is calculated based on Formula (8). From Formula (7), it can be seen that $W_2$=247.5 ms. Furthermore, the gain K is determined to be 0.8 in step ST62. Furthermore, the deviation DM is DM=0.05 mm according to Formula (10). Therefore, by substituting these values into Formula (8), the pulse width $W_3$ can be calculated as described below.

$$W_3 = W_2 - W_2 * K * DM = 247.5 \text{ ms} - 247.5 \text{ ms} * 0.8 * 0.05 = 237.6 \text{ ms} \quad (11)$$

Therefore, in operation $T_2$, the pulse width $W_2$=247.5 ms was used, but by the process of step ST6, the pulse width $W_3$ corresponding to the next operation $T_3$ is calculated as $W_3$=237.6 ms. FIG. 10 depicts the calculated pulse width $W_3$ (=237.6 mm). Once the pulse width $W_3$ has been calculated, the process proceeds to step ST7.

In step ST7, the processor 32 determines if the table 300 has reached the target height. Here, it is assumed that the table 300 has not reached the target height. Therefore, the process returns to step ST1.

In step ST1, the processor 32 waits for a tap operation $T_3$ (see FIG. 10) of the down button 13. When the operator 401 taps the down button 13 in a tap operation $T_3$, the process proceeds to step ST2.

In step ST2, as depicted in FIG. 6, an operation signal SB4 for lowering the height of the table 300 by the target change amount TW is output from the operation panel 10 and input to the converter 31. Upon receiving the operation signal SB4, the converter 31 converts the voltage of the operation signal SB4 and outputs a voltage-converted signal SB41. The processor 32 generates a control signal SC22 including a pulse width $W=W_3$ expressed by Formula (11) based on the signal SB41 from the converter 31. FIG. 10 depicts that the pulse width $W_3$ (=237.6 ms) is used as the pulse width W when the tap operation $T_3$ is executed. After the control signal SC22 including the pulse width $W(=W_3)$ is generated, the process proceeds to step ST3.

In step ST3, the height of the table 300 is fine adjusted based on the control signal SC22. Specifically, as depicted in FIG. 6, the control signal SC22 is supplied to a buffer 34, and after a prescribed process is performed in the buffer 34, a control signal SC221 is supplied to the TFT 35. When the control signal SC221 is supplied, the TFT 35 is turned on and the valve 29 is opened. At this time, the TFT 35 maintains the ON state for a period of time corresponding to the pulse width $W_3$ (=237.6 ms). Therefore, an amount of oil corresponding to the pulse width $W_3$ is discharged from the cylinder 21 to the oil tank 24. Therefore, the cylinder 21 moves in the direction of arrow B, and the subject support unit 303 moves down, so that the height of the table 300 is fine adjusted.

In step ST4, the display unit 16 displays the current height of the table 300 corresponding to the operation $T_3$, based on the analog signal SE from the potentiometer 42. Once the current height of the table 300 has been displayed, the process proceeds to step ST5.

In step ST5, the processor 32 calculates the actual descending amount D of the table 300 based on the digital signal SE received from the ADC 36. FIG. 10 depicts the descending amount $D=D_3$ of the table 300 corresponding to the operation $T_3$. Here, $D_3$=0.5 mm. After the descending amount $D=D_3$ (=0.5 mm) is calculated, the process proceeds to step ST6.

In step ST6, the processor 32 uses the pulse width $W_3$ used in the tap operation $T_3$ to calculate a pulse width $W_4$ to be used when lowering the table during the next tap operation $T_4$. The pulse width $W_4$ is calculated using Formula (12) below.

$$W_4 = W_3 - W_3 * K * DM \tag{12}$$

$W_4$: pulse width used in the next operation $T_4$ $W_3$: pulse width used in operation $T_3$ K: Gain DM: Deviation calculated in operation $T_3$ Note that when calculating the pulse width $W_4$ using the formula (12), the pulse width $W_4$ can be calculated based on the flow depicted in FIG. 11, similarly to the pulse width $W_2$ and $W_3$. Therefore, a method for calculating the pulse width $W_4$ will be described with reference to FIG. 11.

In step ST61, the processor 32 calculates the deviation DM, which is the difference between the descending amount D calculated in step ST5 and the target change amount TW. The deviation DM is expressed by the following Formula (13).

$$DM = D_3 - TW \tag{13}$$

$D_3$: descending amount when operation $T_3$ is executed

TW: target change amount

In the present embodiment, the target change amount TW is 0.5 mm. Furthermore, the descending amount $D_3$ caused by operation $T_3$ is $D_3$=0.5 mm. Therefore, the deviation DM is expressed by the following Formula (14).

$$DM = D_3 - TW = 0.5 - 0.5 = 0 \text{ (mm)} \tag{14}$$

After calculating the deviation DM, the process proceeds to step ST62. In step ST62, the processor 32 determines the gain value K based on the deviation DM. In the present embodiment, as described above, the gain K is determined based on the following three conditions (4) to (6).

$$DM > 0.15\text{: } K = 0.5 \tag{4}$$

$$0.15 \geqq DM \geqq -0.05\text{: } K = 0.8 \tag{5}$$

$$-0.05 > DM\text{: } K = 1.8 \tag{6}$$

Here, DM is calculated as DM=0 mm as depicted in Formula (14). Therefore, since DM satisfies condition (5), the processor 32 determines that the gain K is K=0.8. After the gain K is determined, the process proceeds to step ST63.

In step ST63, the pulse width $W_4$ is calculated based on Formula (12). From Formula (11), it can be seen that $W_3$=237.6 ms. Furthermore, the gain K is determined to be 0.8 in step ST62. Furthermore, the deviation DM is DM=0 mm according to Formula (14). Therefore, by substituting these values into Formula (12), the pulse width $W_4$ can be calculated as described below.

$$W_4 = W_3 - W_3 * K * DM = 237.6 \text{ ms} - 237.6 \text{ ms} * 0.8 * 0 = 237.6 \text{ ms} \tag{15}$$

Therefore, the pulse width $W_4$ corresponding to the next operation $T_4$ is calculated as $W_4$=237.6 ms. FIG. 10 depicts the calculated pulse width $W_4$ (=237.6 mm). Once the pulse width $W_4$ has been calculated, the process proceeds to step ST7.

In step ST7, the processor 32 determines if the table 300 has reached the target height. Here, it is assumed that the table 300 has not reached the target height. Therefore, the process returns to step ST1.

In step ST1, the processor 32 waits for a tap operation $T_4$ (see FIG. 10) of the down button 13. When the operator 401 taps the down button 13 $T_4$, the process proceeds to step ST2.

In step ST2, as depicted in FIG. 6, an operation signal SB4 for lowering the height of the table 300 by the target change amount TW is output from the operation panel 10 and input to the converter 31. Upon receiving the operation signal SB4, the converter 31 converts the voltage of the operation signal SB4 and outputs a voltage-converted signal SB41. The processor 32 generates a control signal SC22 including a pulse width $W=W_4$ expressed by Formula (15) based on the signal SB41 from the converter 31. FIG. 10 depicts that the pulse width $W_4$ (=237.6 ms) is used as the pulse width W when the tap operation $T_4$ is executed. After the control signal SC22 including the pulse width $W(=W_4)$ is generated, the process proceeds to step ST3.

In step ST3, the height of the table 300 is fine adjusted based on the control signal SC22. Specifically, as depicted in FIG. 6, the control signal SC22 is supplied to a buffer 34, and after a prescribed process is performed in the buffer 34, a control signal SC221 is supplied to the TFT 35. When the control signal SC221 is supplied, the TFT 35 is turned on and the valve 29 is opened. At this time, the TFT 35 maintains the ON state for a period of time corresponding to the pulse width $W_4$ (=237.6 ms). Therefore, an amount of oil corresponding to the pulse width $W_2$ is discharged from the cylinder 21 to the oil tank 24. Therefore, the cylinder 21 moves in the direction of arrow B, and the subject support unit 303 moves down, so that the height of the table 300 is fine adjusted.

In step ST4, the display unit 16 displays the current height of the table 300 corresponding to the operation $T_4$, based on the analog signal SE from the potentiometer 42. Once the current height of the table 300 has been displayed, the process proceeds to step ST5.

In step ST5, the processor 32 calculates the actual descending amount D of the table 300 based on the digital signal SE received from the ADC 36. FIG. 10 depicts the descending amount $D=D_4$ of the table 300 corresponding to the operation $T_3$. Here, $D_4$=0.5 mm. After the descending amount $D=D_4$ (=0.5 mm) is calculated, the process proceeds to step ST6.

In step ST6, the processor 32 uses the pulse width $W_4$ used in the tap operation $T_4$ to calculate a pulse width $W_5$ to be used when lowering the table during the next tap operation $T_5$. The pulse width $W_5$ is calculated using Formula (16) below.

$$W_5 = W_4 - W_4 * K * DM \tag{16}$$

$W_5$: pulse width used in the next operation $T_5$
$W_4$: pulse width used in operation $T_4$
K: Gain
DM: Deviation calculated in operation $T_4$ Note that when calculating the pulse width $W_5$ using the formula (16), the pulse width $W_5$ can be calculated based on the flow depicted in FIG. 11, similarly to the pulse width $W_2$ to $W_4$. Therefore, a method for calculating the pulse width $W_5$ will be described with reference to FIG. 11.

In step ST61, the processor 32 calculates the deviation DM, which is the difference between the descending amount D calculated in step ST5 and the target change amount TW. The deviation DM is expressed by the following Formula (17).

$$DM = D_4 - TW \tag{17}$$

$D_4$: descending amount when operation $T_4$ is executed
TW: target change amount In the present embodiment, the target change amount TW is 0.5 mm. Furthermore, the descending amount $D_4$ caused by operation $T_4$ is $D_4$=0.5 mm. Therefore, the deviation DM is expressed by the following Formula (18).

$$DM = D_4 - TW = 0.5 - 0.5 = 0 \text{ (mm)} \tag{18}$$

After calculating the deviation DM, the process proceeds to step ST62. In step ST62, the processor 32 determines the gain value K based on the deviation DM. In the present embodiment, as described above, the gain K is determined based on the following three conditions (4) to (6).

$$DM > 0.15\text{: } K = 0.5 \tag{4}$$

$$0.15 \geqq DM \geqq -0.05\text{: } K = 0.8 \tag{5}$$

$$-0.05 > DM\text{: } K = 1.8 \tag{6}$$

Here, DM is calculated as DM=0 mm as depicted in Formula (18). Therefore, since DM satisfies condition (5), the processor 32 determines that the gain K is K=0.8. After the gain K is determined, the process proceeds to step ST63.

In step ST63, the pulse width $W_5$ is calculated based on Formula (16). From Formula (15), it can be seen that $W_4$=237.6 ms. Furthermore, the gain K is determined to be 0.8 in step ST62. Furthermore, the deviation DM is DM=0 mm according to Formula (18). Therefore, by substituting these values into Formula (16), the pulse width $W_5$ can be calculated as described below.

$$W_5 = W_4 - W_4 * K * DM = 237.6 \text{ ms} - 237.6 \text{ ms} * 0.8 * 0 = 237.6 \text{ ms} \tag{19}$$

Therefore, the pulse width $W_5$ corresponding to the next operation $T_5$ is calculated as $W_5$=237.6 ms.

Similarly, the pulse width to be used in the next tapping operation is calculated each time a tapping operation is executed to lower the height of the table 300. In the above description, an example of calculating pulse widths $W_2$, $W_3$, $W_4$, and $W_5$ was described. If the pulse width to be calculated is represented as "$W_{i+1}$", the pulse width $W_{i+1}$ can be calculated by the following Formula (20).

$$W_{i+1} = W_i - W_i * K * DM \tag{20}$$

Here, $W_{i+1}$: pulse width used in the next operation $T_{1+1}$
$W_i$: pulse width used in operation $T_1$
K: Gain
DM: Deviation calculated in operation $T_i$ For example, when an operation $T_p$ is executed, the pulse width $W_{p+1}$ used in the next operation $T_{p+1}$ is calculated by the following formula, where i=p is substituted for i in Formula (20).

$$W_{p+1} = W_p - W_p * K * DM \tag{21}$$

Here, $W_{p+1}$: pulse width used in the next operation $T_{p+1}$
$W_p$: pulse width used in the operation $T_p$ K: Gain DM: Deviation calculated in operation $T_p$ Therefore, each time an operation is executed, a pulse width $W_{i+1}$ for matching the table descending amount to (or approaching) the target change amount can be calculated based on Formula (20). Furthermore, when a determination is made in step ST7 that the table 300 has reached the target height, the flow ends.

In the present embodiment, when fine adjusting the height of the table 300, the operator 401 uses the buttons on the operation panel 10 to execute the fine adjust operation of the table 300. When the operator 401 executes a fine adjust operation to lower the height of the table 300 by a target change amount, the height of the table 300 is fine adjusted to be lowered in response to the operation of the operator 401. On the other hand, the processor 32 adjusts the pulse width based on the deviation DM between the actual descending amount D of the table 300 and the target change amount TW. In the present embodiment, the gain value K is determined based on the deviation DM, so the pulse width for making the deviation DM zero (or making smaller) can be calculated. Furthermore, when the operator 401 executes the next operation, the height of the table 300 is fine adjusted based on the calculated pulse width. Therefore, even if the descending amount D of the table 300 initially differs from the target change amount TW when fine adjustment of the height of table 300 begins, the descending amount D of table 300 can be brought closer to the target change amount TW by calculating the pulse width based on the deviation DM as described above, and ultimately, the descending amount D can be made to match the target change amount TW. Once the descending amount D coincides with the target change amount TW, the descending amount stabilizes, and thereafter, the descending amount of the table 300 can be made to (substantially) match the target change amount TW. Therefore, the actual descending amount D is stable in response to the operation of the operator 401, so the workload of the operator 401 can be reduced when adjusting the height of the table 300.

Figure 12:
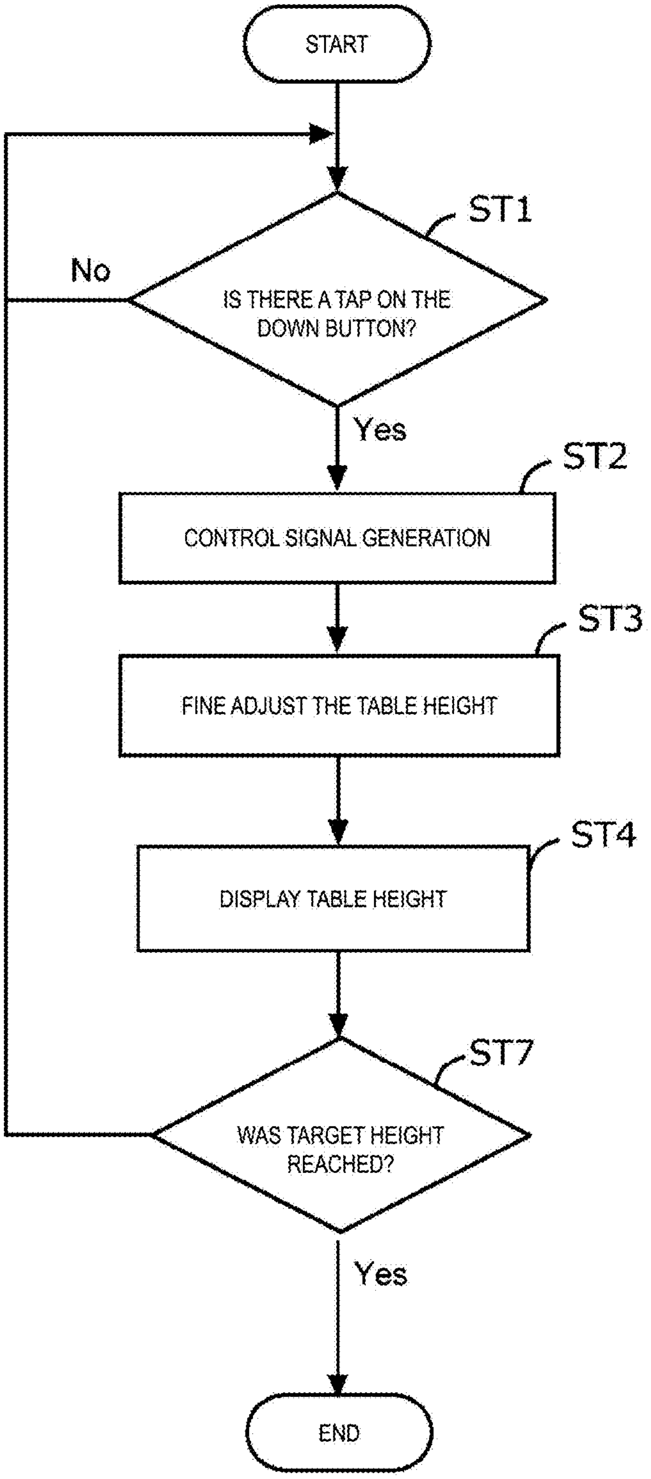
FIG. 12 depicts a flow when the pulse width is set to a fixed value.

In the flow of FIG. 9 executed in the present embodiment, the gain value K is determined in accordance with the deviation DM, and the pulse width is calculated (see step ST). For reference, however, FIG. 12 depicts a flow in the case where the pulse width is set to a fixed value. In the flow of FIG. 12, the pulse width is a fixed value, so step ST5 for calculating the descending amount required for calculating the pulse width and step ST6 for calculating the pulse width are not performed. Therefore, the pulse width cannot be set to an optimum value, and as a result, the descending amount of the table cannot be made to match the target change amount, as depicted in FIG. 8. In contrast, in the present embodiment, steps ST5 and ST6 are performed, so even if the descending amount of the table does not match the target change amount, the value of gain K is determined in accordance with the deviation DM and the pulse width is calculated, so the descending amount of table 300 can be quickly made to (substantially) match the target change amount TW.

In order to clarify the effect of the present embodiment, the relationship between the number of tap operations and the amount of movement of the table height was calculated. The calculation results are depicted in FIG. 13.

Figure 13:
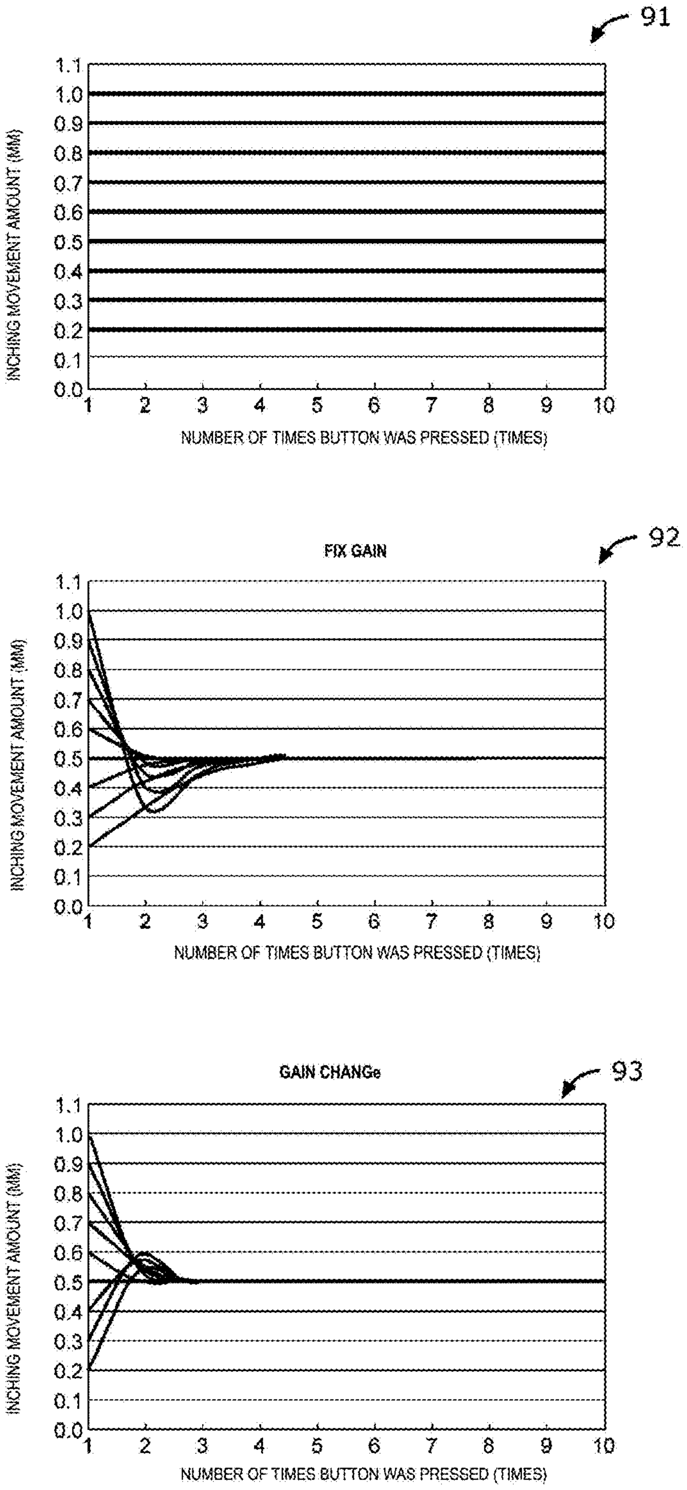
FIG. 13 is a diagram depicting calculation results.

FIG. 13 depicts graphs 91, 92, and 93. Graphs 91 to 93 depict the relationship between the number of tap operations and the amount of movement of the table height when the initial value of the table movement is 0.2 (mm), 0.3 (mm), 0.4 (mm), 0.5 (mm), 0.6 (mm), 0.7 (mm), 0.8 (mm), 0.9 (mm), and 1.0 (mm).

Graph 91 depicts the relationship between the number of tapping operations and the amount of movement of the table height when the pulse width is a fixed value. It can be seen that when the pulse width is set to a fixed value, the amount of movement does not change from the initial value no matter how many times the tap operation is repeated.

Graph 92 depicts the relationship between the number of tapping operations and the amount of movement of the table height when proportional control is adopted with a fixed gain K. When proportional control with a fixed gain K is adopted, the movement amount converges from the initial value to the target movement amount of 0.5 mm by repeatedly executing the tap operation, but the tap operation must be repeated 4 to 5 times until convergence occurs.

Graph 93 depicts the relationship between the number of tap operations and the amount of movement of the table height when the method of the present embodiment is adopted such that the gain K is determined based on the amount of deviation DM. When the method of the present embodiment is adopted, the movement amount clearly converges from the initial value to the target movement amount of 0.5 mm by repeatedly executing the tap operation three times.

Therefore, graphs 91 to 93 show that by adopting the method of the present embodiment, even if the descending amount of the table 300 does not match the target change amount, the descending amount of the table will quickly (substantially) match the target change amount TW.

FIG. 10 depicts an example in which operations $T_1$ to $T_{p+1}$ for fine adjusting the height of the table 300 are successively executed so that the table 300 is lowered by the descending amount D. However, between operations $T_1$ to $T_{p+1}$, another operation may be executed to adjust the height of the table (see FIG. 14).

Figure 14:
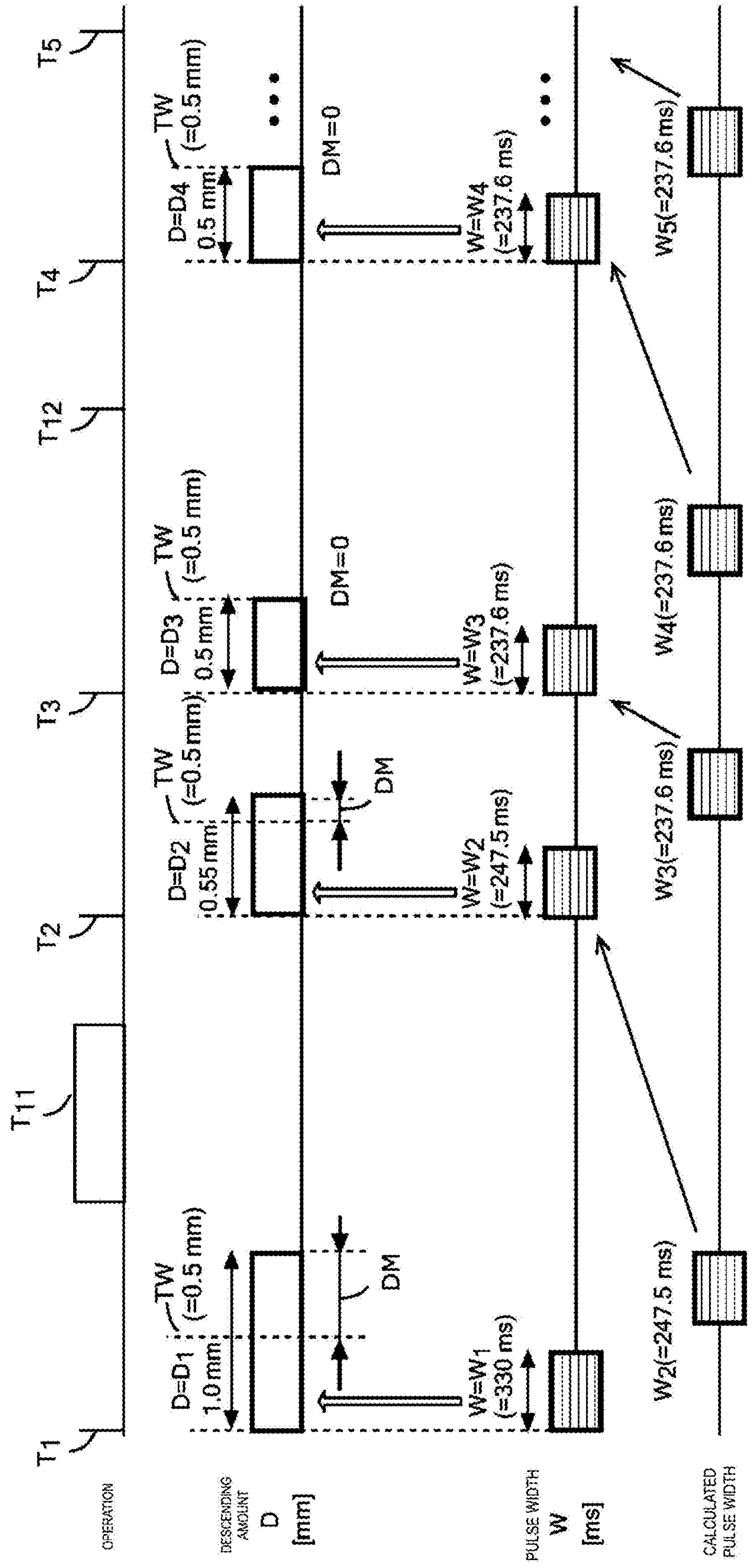
FIG. 14 is a diagram depicting an example where another operation for adjusting the height of the table is executed between operations $T_1$ to $T_5$.

FIG. 14 is a diagram depicting an example where another operation for adjusting the height of the table is executed between operations $T_1$ to $T_5$. FIG. 14 depicts an example in which an operation U11 for continuously lowering the table 300 is executed between operations $T_1$ and $T_2$, and an operation U12 for raising the table 300 by a target change amount TV (see FIG. 3) is executed between operations $T_3$ and $T_4$.

In this manner, even if other operations U11 and U12 are executed between operations $T_1$ to $T_5$, the pulse widths $W_2$ to $W_5$ can be calculated by focusing only on operations $T_1$ to $T_5$, calculating the deviation DM for operations $T_1$ to $T_5$ using the procedures described above, and determining the value of gain K based on the deviation DM. Therefore, the descending amount D can be quickly made to match the target change amount TW.

In the first embodiment, an example was described where the descending amount D of the table 300 is made to match the target change amount TW (see FIG. 4), but the present invention can also be applied to a case in which the ascending amount of the table 300 is made to match the target change amount TV (see FIG. 3). When raising the table 300, the deviation DM between the ascending amount of table and the target change amount TV is calculated, and the gain value K is determined based on the deviation DM, and thereby the pulse width for causing the ascending amount of the table to match the target change amount TV (or approach the target change amount TV).

Figure 15:
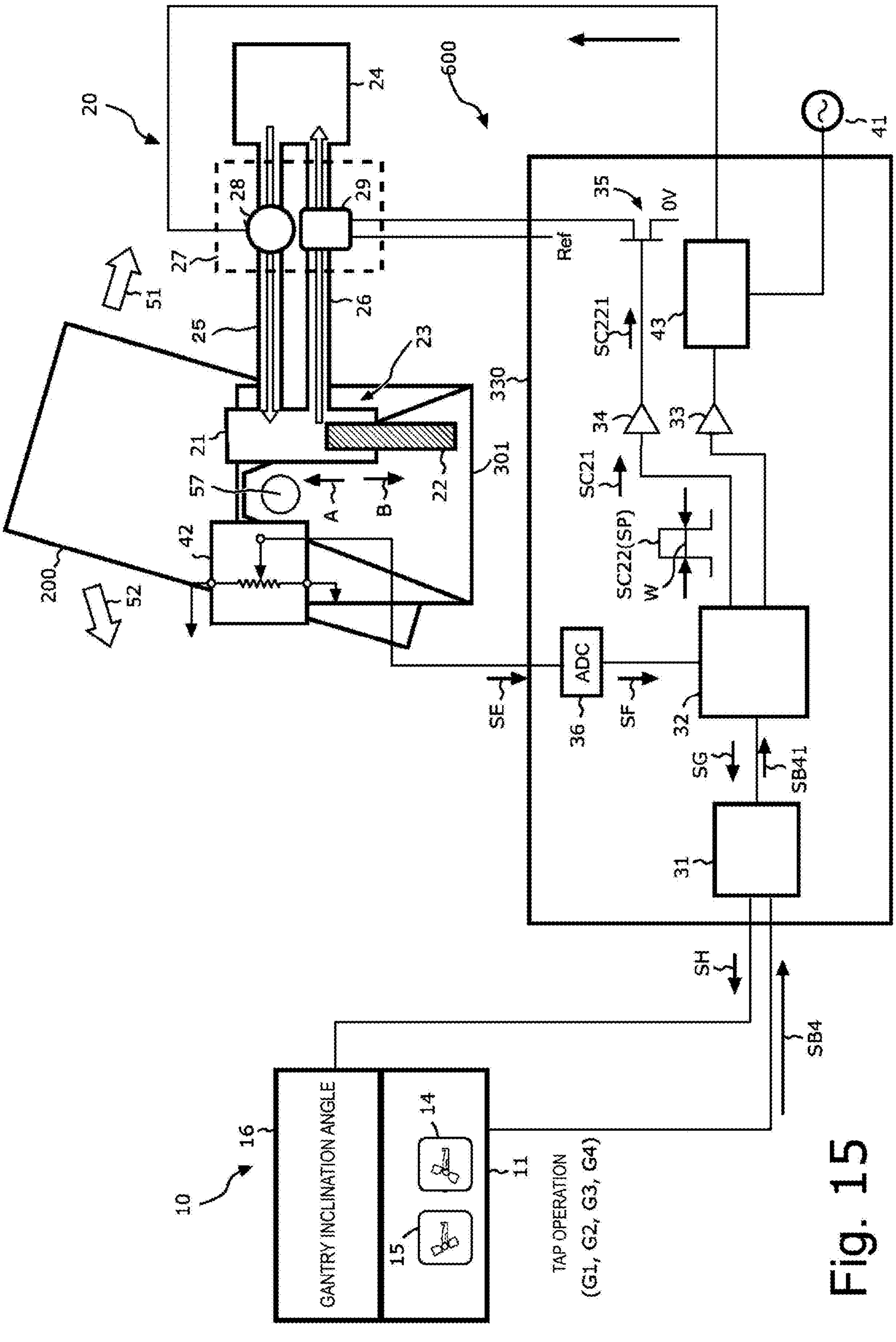
FIG. 15 is an explanatory diagram depicting a case where a forward inclination button 14 is tapped.

In the second embodiment, a case will be described in which the CT system has a function of adjusting the inclination angle of the gantry 200. FIG. 15 is a block diagram of the gantry 200 and a gantry control device 600 that controls the inclination angle of the main body of the gantry.

Incidentally, the gantry control device 600 of the second embodiment is basically the same as the table control device 500 described in the first embodiment. Therefore, when describing the second embodiment, the differences from the first embodiment will be mainly be described.

The gantry control device 600 has a hydraulic device 20. The hydraulic device 20 includes a unit 23 having a cylinder 21 and a piston 22, an oil tank 24, a supply pipe 25, a discharge pipe 26, and an oil amount adjustment unit 27. The hydraulic device 20 is housed inside the gantry 200, but in FIG. 15, structural elements other than the unit 23 are depicted outside the gantry 200 in order to make the structural elements of the hydraulic system 20 easier to observe. When the cylinder 21 moves in the direction of arrow B toward the piston 22, the gantry 200 inclines toward the rear side 52 around the rotation axis 57. On the other hand, when the cylinder 21 moves in the direction of arrow A relative to the piston 22, the gantry 200 inclines toward the front side 51 around the rotation axis 57. Note that the structures of the unit 23, oil tank 24, supply pipe 25, discharge pipe 26, and oil amount adjustment unit 27 of the hydraulic device 20 are the same as those of the hydraulic device described in the first embodiment, so descriptions that overlap with the first embodiment will be omitted.

Furthermore, the gantry control device 600 also includes an operation panel 10 and a control board 330. The structure of the operation panel 10 is the same as that of the operation panel 10 described in the first embodiment. In addition, the control board 330 of the second embodiment includes a relay 43 that supplies an AC signal from an AC source 41 to the pump 28, but the remaining configuration is the same as the control board 30 of the first embodiment.

Figure 16:
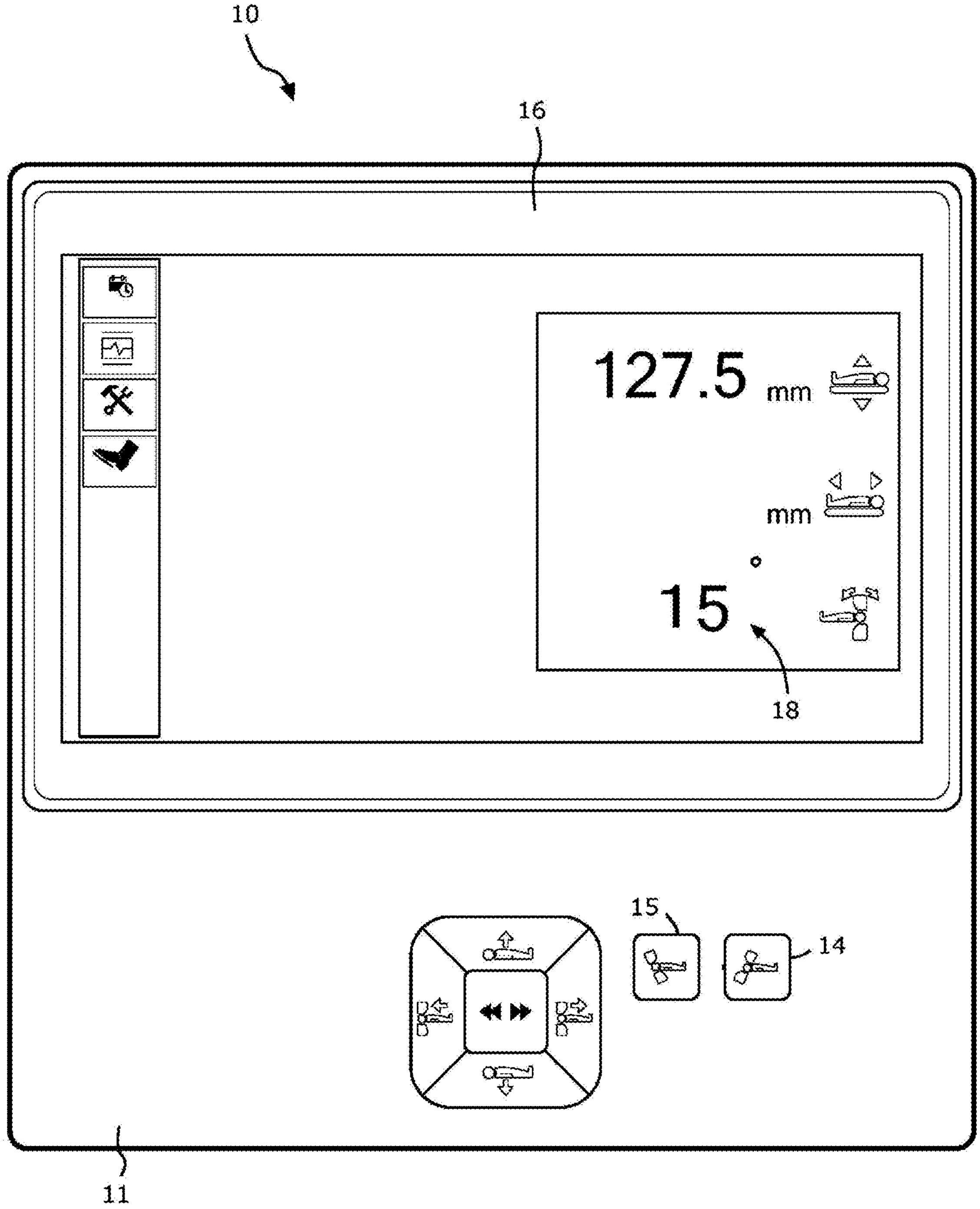
FIG. 16 is an explanatory diagram of an operation panel 10 according to a second embodiment.

FIG. 16 is an explanatory diagram of an operation panel 10 according to a second embodiment. In FIG. 16, only the parts related to the operation of the CT system of the second embodiment are denoted by reference numerals and will be described.

The operation panel 10 includes a forward inclination button 14 and a backward inclination button 15 for inclining the gantry 200. The forward inclination button 14 is a button for inclining the gantry 200 to the front side 51, and the backward inclination button 15 is a button for inclining the gantry 200 to the rear side 52.

When the operator 401 wishes to roughly adjust the inclination angle of the gantry 200, the operator 401 presses and holds the forward inclination button 14 or the backward inclination button 15. For example, if there is desire to continuously cause the gantry 200 to incline to the front side 51, the operator 401 long presses the forward inclination button 14. When the forward inclination button 14 is long pressed, the gantry 200 continuously inclines to the front side 51 while the forward inclination button 14 is being long pressed by the operator 401. On the other hand, when there is desire to continuously cause the gantry 200 to incline toward the rear side 52, the operator 401 long presses the backward inclination button 15. When the backward inclination button 15 is long pressed, the gantry 200 continuously inclines to the rear side 52 while the backward inclination button 15 is being long pressed by the operator 401.

Figure 17:
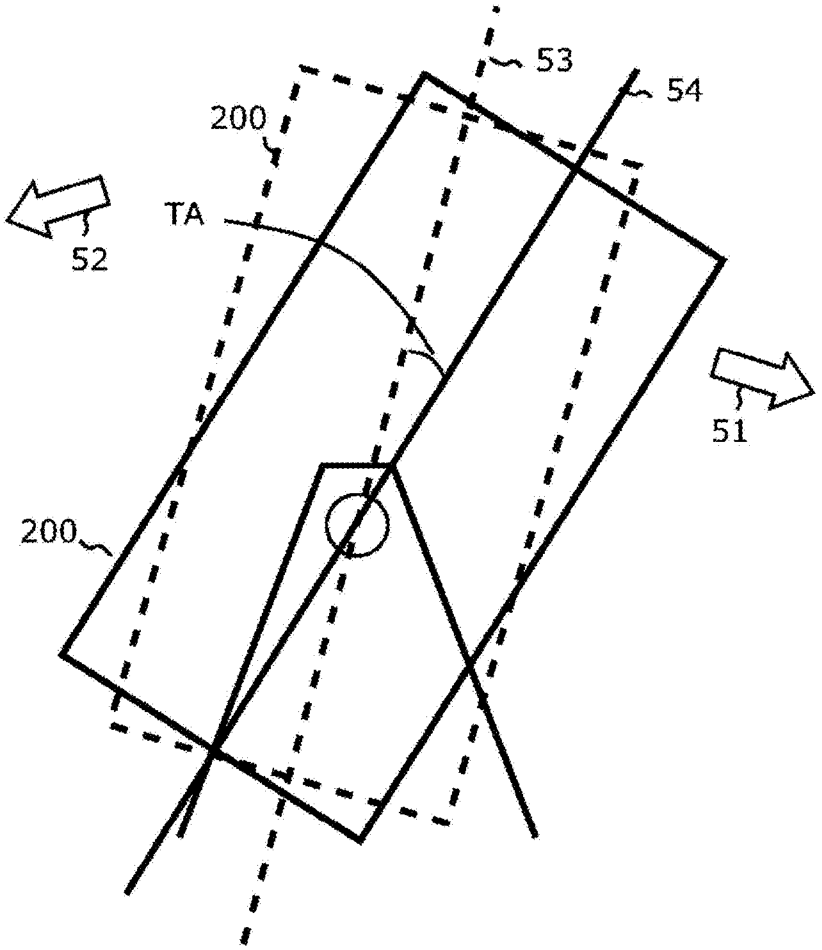
FIG. 17 is an explanatory diagram depicting a case where a forward inclination button 14 is tapped.

Furthermore, when the operator 401 wishes to fine adjust the inclination angle of the gantry 200, the operator 401 performs a tapping operation in which the operator presses the forward inclination button 14 or the backward inclination button 15 and immediately releases the button 14 or 15. FIG. 17 is an explanatory diagram depicting a case where a forward inclination button 14 is tapped. In FIG. 17, the gantry 200 before the tapping operation is depicted by a dashed line, and the gantry 200 after the tapping operation is depicted by a solid line. The inclination angle of the gantry 200 changes from inclination angle 53 to inclination angle 54 with a single tap operation. In other words, the gantry 200 is set so that the inclination angle changes toward the front side 51 by the target change amount TA in response to a single tap operation. In FIG. 17, the target change amount TA is exaggerated to facilitate understanding, but in reality, the target change amount TA is a value where TA is approximately 0.1 (degrees) to 0.5 (degrees). Therefore, the operator 401 can fine control the inclination angle of the gantry 200 by executing the forward inclination button 14.

Figure 18:
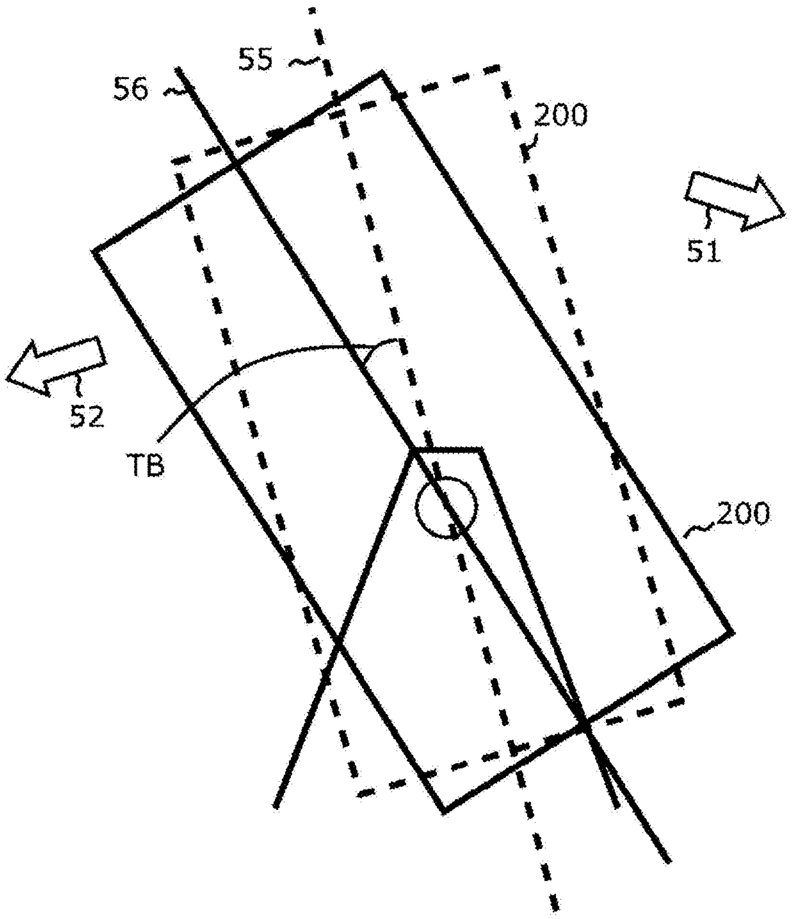
FIG. 18 is an explanatory diagram depicting a case where a backward inclination button 15 is tapped.

On the other hand, FIG. 18 is an explanatory diagram of a case where the backward inclination button 15 is tapped. In FIG. 18, the gantry 200 before the tapping operation is depicted by a dashed line, and the gantry 200 after the tapping operation is depicted by a solid line. The inclination angle of the gantry 200 changes from inclination angle 55 to inclination angle 56 with a single tap operation. In other words, the gantry 200 is set so that the inclination angle changes toward the back side 52 by the target change amount TB in response to a single tap operation. In FIG. 18, the target change amount TB is exaggerated to facilitate understanding, but in reality, the target change amount TB is a value where TB is approximately 0.1 (degrees) to 0.5 (degrees). Therefore, the operator 401 can fine control the inclination angle of the gantry 200 by executing the backward inclination button 15.

Incidentally, the target change amount TA when inclining the gantry 200 toward the front side 51 is the same as the target change amount TB when inclining the gantry 200 toward the rear side 52 (or in other words, TA=TB). However, TA≠TB is also possible.

Returning to FIG. 16, the description is continued. The display unit 16 of the operation panel 10 includes a display region 18. The display region 18 is a region that displays the current inclination angle of the gantry. Therefore, the operator 401 can adjust the inclination angle of the gantry 200 while checking the current inclination angle of the gantry 200 on the display unit 16 by executing the forward inclination button 14 or the backward inclination button 15. Furthermore, the gantry control device 600 includes a potentiometer 42. The potentiometer 42 measures the inclination angle of the gantry 200.

The gantry control device 600 is configured as described above. When the operator 401 executes an operation for fine adjusting the inclination angle of the gantry 200, ideally, the inclination angle of the gantry 200 changes by a target change amount TA or TB (for example, 0.5 degrees). However, depending on the environment in which the gantry 200 is used (such as the temperature, humidity, and the like in the scan room), the actual change amount in the inclination angle of the gantry 200 may deviate from the target change amount TA or TB.

In this manner, even if the gantry inclination angle does not match the target change amount TA or TB, a pulse width that can make the deviation DM zero (or approach zero) can be calculated by adjusting the gain K based on the deviation DM, as described in the first embodiment.

In the first and second embodiments, a CT system is used as an example of a medical device. However, the present invention is not limited to CT systems, and can be applied to medical devices that require the use of cylinders and pistons to adjust the movement of a movable body (for example, MRI devices, PET-CT devices, PET-MRI devices, radiation therapy devices, and the like).

The invention claimed is:

1. A movable body control device, comprising:

a unit including a cylinder and a piston, at least a portion of the piston being provided in the cylinder, and configured to move one of the cylinder and the piston relative to the other by adjusting an amount of a working fluid in the cylinder;

a movable body that moves in response to relative movement of the cylinder and the piston;

a control unit that generates a control signal including a first pulse width corresponding to a target change amount so that the movable body moves by the target change amount, based on a first operation signal input by a user operation, the first operation signal provided for moving the movable body by the target change amount; and a fluid amount adjusting unit that adjusts the amount of the working fluid contained in the cylinder based on the first pulse width;

wherein the control unit determines an amount of movement of the movable body by adjusting the amount of working fluid in the cylinder;

determines a gain value based on a deviation between the amount of movement of the movable body and the target amount of change;

calculates a second pulse width based on the deviation and the determined gain value; and generates a control signal including the second pulse width when a second operation signal for moving the movable body by a target change amount is input after the first operation signal;

and the fluid amount adjusting unit adjusts the amount of working fluid in the cylinder based on the second pulse width.

2. The movable body control device according to claim 1, wherein the control unit determines the gain value based on which of a plurality of conditions are satisfied by the deviation.

3. The movable body control device according to claim 2, wherein the display control unit determines the gain value based on which of three conditions are satisfied by the deviation.

4. A movable body control device as described in claim 3, wherein the control unit determines that the gain value is a first value when the deviation satisfies a first condition of the three conditions, determines the gain value to be a second value when the deviation satisfies a second condition of the three conditions, and determines the gain value to be a third value when the deviation satisfies a third condition of the three conditions.

5. The movable body control device according to claim 1, wherein the movable body control device is used for a table of a medical device, the movable body is a subject support unit of a table, and the first operation signal and the second operation signal are operation signals for changing the height of the table by the target change amount.

6. The movable body control device according to claim 5, wherein the target change amount is a target change amount when the table is lowered.

7. The movable body control device according to claim 5, wherein the target change amount is a target change amount when the table is raised.

8. The movable body control device according to claim 1, wherein the movable body control device is used for a gantry of a medical device, the movable body is the gantry, and the first operation signal and the second operation signal are operation signals for changing the inclination angle of the gantry by the target change amount.

9. The movable body control device according to claim 8, wherein the target change amount is a target change amount when the gantry is inclined toward the front side of the gantry.

10. The movable body control device according to claim 8, wherein the target change amount is a target change amount when the gantry is inclined toward a rear surface of the gantry.

11. The movable body control device according to claim 1, wherein the fluid amount adjusting unit includes:

a pump for supplying the working fluid to the cylinder; and a valve for discharging the working fluid from the cylinder.

12. The movable body control device according to claim 11, wherein the pump supplies a quantity of working fluid to the cylinder corresponding to the second pulse width.

13. The movable body control device according to claim 11, wherein the valve supplies a quantity of working fluid from the cylinder corresponding to the second pulse width.

14. The movable body control device according to claim 1, wherein the movable body control device includes a potentiometer that outputs an analog signal expressing a voltage corresponding to the movement of the movable body;

the control unit includes an ADC that converts an analog signal from the potentiometer into a digital signal; and the control unit calculates an amount of movement of the movable body based on the digital signal from the ADC.

15. The movable body control device according to claim 1, wherein the display control unit determines a gain value based on a deviation between an amount of movement of the movable body and the target change amount every time an operation signal is input for moving the movable body by a target change amount of change; and calculates a pulse width to be used when the next operation signal is input based on the deviation and the determined gain value.

16. A non-transitory computer-readable storage medium included in a movable body control device or capable of communicating with the movable body control device, wherein the moveable body control device includes:

a unit including a cylinder and a piston, at least a portion of the piston being provided in the cylinder, and configured to move one of the cylinder and the piston relative to the other by adjusting an amount of a working fluid in the cylinder;

a movable body that moves in response to relative movement of the cylinder and the piston;

a control unit that generates a control signal including a first pulse width corresponding to a target change amount so that the movable body moves by the target change amount, based on a first operation signal input by a user operation, the first operation signal provided for moving the movable body by the target change amount; and a fluid amount adjusting unit that adjusts the amount of the working fluid contained in the cylinder based on the first pulse width; wherein the control unit includes one or more processors;

the instructions contained in the memory, when executed by the one or more processors, cause the one or more processors to:

determine an amount of movement of the movable body by adjusting the amount of working fluid in the cylinder;

determine a gain value based on a deviation between the amount of movement of the movable body and the target change amount;

calculate a second pulse width based on the deviation and the determined gain value; and generate a control signal including the second pulse width when a second operation signal for moving the movable body by a target change amount is input after the first operation signal; and the fluid amount adjusting unit adjusts the amount of working fluid in the cylinder based on the second pulse width.

* * * * *